US008158370B2

(12) United States Patent
Liu et al.

(10) Patent No.: US 8,158,370 B2
(45) Date of Patent: Apr. 17, 2012

(54) *ANAPLASMA PHAGOCYTOPHILUM (APH)* ANTIGENS AND ANTIBODIES SPECIFIC FOR *ANAPLASMA*

(75) Inventors: Jiayou Liu, Scarborough, ME (US); Ramaswamy Chandrashekar, Scarborough, ME (US)

(73) Assignee: IDEXX Laboratories, Inc., Westbrook, MA (US)

( * ) Notice: Subject to any disclaimer, the term of this patent is extended or adjusted under 35 U.S.C. 154(b) by 0 days.

(21) Appl. No.: 12/745,047

(22) PCT Filed: Nov. 21, 2008

(86) PCT No.: PCT/US2008/084391
§ 371 (c)(1),
(2), (4) Date: Sep. 8, 2010

(87) PCT Pub. No.: WO2009/070507
PCT Pub. Date: Jun. 4, 2009

(65) Prior Publication Data
US 2011/0008380 A1 Jan. 13, 2011

Related U.S. Application Data

(60) Provisional application No. 60/990,420, filed on Nov. 27, 2007.

(51) Int. Cl.
*G01N 33/53* (2006.01)
(52) U.S. Cl. ......... 435/7.1; 435/7.2; 435/7.32; 435/7.92
(58) Field of Classification Search .................. None
See application file for complete search history.

(56) References Cited

U.S. PATENT DOCUMENTS

| | | | |
|---|---|---|---|
| 5,192,679 A | 3/1993 | Dawson et al. |
| 5,401,656 A | 3/1995 | Dawson et al. |
| 5,413,931 A | 5/1995 | Dawson et al. |
| 5,726,010 A | 3/1998 | Clark |
| 5,789,176 A | 8/1998 | Dawson et al. |
| 5,869,335 A | 2/1999 | Munderloh et al. |
| 5,928,879 A | 7/1999 | Dumler et al. |
| 5,955,359 A | 9/1999 | Dumler et al. |
| 5,976,791 A | 11/1999 | Mabilat et al. |
| 5,976,860 A | 11/1999 | Coughlin et al. |
| 5,989,848 A | 11/1999 | Dawson |
| 6,015,691 A | 1/2000 | Walker et al. |
| 6,025,338 A | 2/2000 | Barbet et al. |
| 6,034,085 A | 3/2000 | Joshi et al. |
| 6,204,252 B1 | 3/2001 | Murphy et al. |
| 6,207,169 B1 | 3/2001 | Reed et al. |
| 6,231,869 B1 | 5/2001 | Reed et al. |
| 6,277,381 B1 | 8/2001 | Reed et al. |
| 6,284,238 B1 | 9/2001 | Coughlin et al. |
| 6,306,394 B1 | 10/2001 | Murphy et al. |
| 6,306,402 B1 | 10/2001 | Reed et al. |
| 6,355,777 B1 | 3/2002 | Walker et al. |
| 6,392,023 B1 | 5/2002 | Walker et al. |
| 6,403,780 B1 | 6/2002 | Walker et al. |
| 6,458,942 B1 | 10/2002 | Walker et al. |
| 6,964,855 B2 | 11/2005 | O'Connor, Jr. et al. |
| 7,439,321 B2 | 10/2008 | O'Connor, Jr. et al. |
| 7,696,310 B2 | 4/2010 | O'Connor, Jr. et al. |
| 2002/0064531 A1 | 5/2002 | Walker et al. |
| 2002/0064535 A1 | 5/2002 | Reed et al. |
| 2002/0068343 A1 | 6/2002 | Reed et al. |
| 2002/0086984 A1 | 7/2002 | Reed et al. |
| 2002/0115840 A1 | 8/2002 | Walker et al. |
| 2002/0132789 A1 | 9/2002 | Barbet et al. |
| 2003/0099639 A1 | 5/2003 | Rikihisa |
| 2005/0124015 A1 | 6/2005 | O'Connor, Jr. et al. |
| 2005/0142557 A1 | 6/2005 | Alleman et al. |
| 2008/0248497 A1 | 10/2008 | Beall et al. |
| 2009/0042222 A1 | 2/2009 | O'Connor, Jr. et al. |
| 2010/0086563 A1 | 4/2010 | Liu |

FOREIGN PATENT DOCUMENTS

| | | |
|---|---|---|
| WO | 98/42740 | 10/1998 |
| WO | 98/49313 | 11/1998 |
| WO | 99/13720 | 3/1999 |
| WO | 99/52370 | 10/1999 |
| WO | 01/85949 | 11/2001 |
| WO | 2009/070507 | 6/2009 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
McBride et al., "Molecular Cloning of the Gene for a Conserved Major Immunoreactive 28-Kilodalton Protein of *Ehrlichia canis*: a Potential Serodiagnostic Antigen", Clinical and Diagnostic Laboratory Immunology, 6:392-399 (1999).
McBride et al., A Conserved, Transcriptionally Action p28 Multigene Locus of *Ehrlichia canis*:, Gene 254:245-252 (2000).
Murphy et al., "Major antigenic proteins of the agent of human granulocytic ehrlichiosis are encoded by members of a multigene family", Infection and Immunity, 66(8):3711-3781 (1998).
Ohashi et al., "Cloning and Characterization of Multigenes Encoding the Immunodominant 30-Kilodalton Major Outer Membrane Proteins of *Ehrlichia canis* and Application of the Recombinant Protein for Serodiagnosis", Journal for Clinical Microbiology, 36:2671-2680 (1998).
Ohashi et al., "Immunodominant Major Outer Membrane Proteins of *Ehrlichia chaffeensis* are Encoded by a Polymorphic Multigene Family", Infection and Immunity, 66:132-139 (1998).
Suksawat et al., "Seroprevalence of *Ehrlichia canis, Ehrlichia equi* and *Ehrlichia risticii* in Sick Dogs from North Carolina and Virginia", Journal Vet. Internal. Med. 14:50 (2000).
Yu et al., "Comparison of *Ehrlichia chaffeenis* Recombinant Porteins for Serologic Diagnosis of Human Monocytotropic Ehrlichiosis", Journal of Clinical Microbiology, 37:2568-2575 (1999).

(Continued)

*Primary Examiner* — Jennifer Graser
(74) *Attorney, Agent, or Firm* — McDonnell Boehnen Hulbert & Berghoff LLP

(57) ABSTRACT

The invention provides methods and compositions for the detection and treatment of *Anaplasma phagocytophilum* and *Anaplasma platys* infection.

21 Claims, No Drawings

OTHER PUBLICATIONS

Yu et al., "Genetic Diversity of the 28-Kilodalton Outer Membrane Protein Gene in Human Isolates of *Ehrlichia chaffeensis*", Journal of Clinical Microbiology, 37:1137-1143 (1999).
Yu et al., "Characterization of the Complete Transcriptionally Active *Ehrlichia chaffeensis* 28 kDa Outer Membrane Protein Multigene Family", Gene, 248:59-68 (2000).
Asanovich et al., "Particial Characterization of Cloned Genes Encoding Immunoreactive Proteins of *Ehrlichia equi* and the agent of Human Granulocytic Ehrlichiosis", Ab. Gen. Meet. American Society for Microbiology, Abstract No. D-22, p. 245 (1996).
Lodes et al., "Serodiagnosis of Human Granulocytic Ehrlichiosis by using Novel Combinations of Immunoreactive Recombinant Proteins", Journal of Clinical Microbiology, vol. 39, No. 7, p. 2466-2476 (2001).
Wormser et al., "False-Positive Lyme Disease Serology in Human Granulocytic Ehrlichiosis", Lancet, 347 p. 981-982 (1996).
Magnarelli, "Coexistence of Antibodies in Tick-Borne Pathogens of Babesiosis, Ehrlichiosis, and Lyme Borrellosis in Human Sera", Journal of Clinical Microbiology, vol. 33, No. 11, p. 3054-3057 (1995).
"Notification List—Notification that new names and new combinations have appeared in vol. 51, part 6, of the IJSEM", 2002, 52, 5-6, International Journal of Systematic and Evolutionary Microbiology.
Communication for European application No. 03719550.0/2401, PCT/US03/010131 dated Apr. 21, 2006.
Greenspan et al., "Defining Epitopes: It's not as Easy as it Seems", Nature Biotech, 17:936-937 (1999).
Bowie et al., "Deciphering the Message in Protein Sequences: Tolerance to Amino Acid Substitutions", Science, 247:1306-1310 (1990).
Blythe et al., "Benchmarking B cell epitope predication: Underperformance of existing methods", Protein Science, 14:246-248 (2005).
Dunning Hotopp et al., "Comparative Genomics of Emerging Human Ehrlichiosis Agents", PLoS Genetics, vol. 2, issue 2, p. 0208-0223 (2006).
UniProtKB/TrEMBL Q2GJG3 dated Oct. 31, 2006.
Alta Bioscience, "FAQ Peptides for antibodies", Last updated Jan. 2010 [retrieved from the internet on Jan. 29, 2010: <URL:http://www.altabioscience.bham.ac.uk/services/peptide/antibodies.shtml>]' section "Waht is the optimum length of a peptide".
Ge et al., "Identification of Novel Surface Proteins of *Anaplasma phagocytophilum* by Affinity Purification and Proteomics", J. Bacteriol. 2007, 189(21):7819-7828.

* cited by examiner

SEQUENCE LISTING

```
<160> NUMBER OF SEQ ID NOS: 12

<210> SEQ ID NO 1
<211> LENGTH: 114
<212> TYPE: PRT
<213> ORGANISM: Anaplasma phagocytophilum
<220> FEATURE:
```

-continued

<221> NAME/KEY: MISC_FEATURE
<222> LOCATION: (52)..(52)
<223> OTHER INFORMATION: X stands for D or G
<220> FEATURE:
<221> NAME/KEY: MISC_FEATURE
<222> LOCATION: (72)..(72)
<223> OTHER INFORMATION: X stands for E or A
<220> FEATURE:
<221> NAME/KEY: MISC_FEATURE
<222> LOCATION: (77)..(77)
<223> OTHER INFORMATION: X stands for F or for no amino acid

<400> SEQUENCE: 1

```
Leu Cys Ala Thr Val His His Ile Tyr Gln Gly Asn Tyr Glu Asp Arg
1               5                   10                  15

Asn Asn Asp Lys Gly Ser Ser Arg Gly Gly Gly Thr Thr Tyr Tyr Pro
            20                  25                  30

Met Thr Met Ser Ala Ser Ala Ser Glu Glu Ser Leu Ser Ser Ile Ile
        35                  40                  45

Ser Glu Gly Xaa Leu Ser Lys Thr Ser Leu Pro Ser Tyr Ser Ala Ala
    50                  55                  60

Thr Ala Thr Gly Thr Gly Asn Xaa Thr Gly Glu Val Xaa Ser His Ser
65                  70                  75                  80

His Ser Ser Gly Lys Ser Ser Ser Lys Pro Glu Ser Arg Pro Glu Ser
                85                  90                  95

Asn Leu Gln Asn Val Val Ala Glu Thr Met Ser Gln Gln Gln Arg Ser
            100                 105                 110

Val Ser
```

<210> SEQ ID NO 2
<211> LENGTH: 175
<212> TYPE: PRT
<213> ORGANISM: Anaplasma phagocytophilum
<220> FEATURE:
<221> NAME/KEY: MISC_FEATURE
<222> LOCATION: (43)..(43)
<223> OTHER INFORMATION: X stands for A or T
<220> FEATURE:
<221> NAME/KEY: MISC_FEATURE
<222> LOCATION: (113)..(113)
<223> OTHER INFORMATION: X stands for D or G
<220> FEATURE:
<221> NAME/KEY: MISC_FEATURE
<222> LOCATION: (133)..(133)
<223> OTHER INFORMATION: X stands for A or E
<220> FEATURE:
<221> NAME/KEY: MISC_FEATURE
<222> LOCATION: (138)..(138)
<223> OTHER INFORMATION: X stands for F or no amino acid

<400> SEQUENCE: 2

```
His Lys Gly Val Asp Ser Asp Arg Lys His Asp Ala Glu Lys Thr Glu
1               5                   10                  15

Glu Lys Lys His Gly Leu Gly Ser Leu Cys Lys Ser Leu Ala Ile Asn
            20                  25                  30

Leu Val Ser Leu Met Gly Thr Ala Leu Val Xaa Thr Pro Ile Ile Leu
        35                  40                  45

Leu Ala Val Val Leu Leu Val Leu Val Pro Val Tyr Leu Leu Cys Ala
    50                  55                  60

Thr Val His His Ile Tyr Gln Gly Asn Tyr Glu Asp Arg Asn Asn Asp
65                  70                  75                  80

Lys Gly Ser Ser Arg Gly Gly Gly Thr Thr Tyr Tyr Pro Met Thr Met
                85                  90                  95

Ser Ala Ser Ala Ser Glu Glu Ser Leu Ser Ser Ile Ile Ser Glu Gly
```

```
                100              105                110
Xaa Leu Ser Lys Thr Ser Leu Pro Ser Tyr Ser Ala Ala Thr Ala Thr
            115                 120                 125

Gly Thr Gly Asn Xaa Thr Gly Glu Val Xaa Ser His Ser His Ser Ser
        130                 135                 140

Gly Lys Ser Ser Lys Pro Glu Ser Arg Pro Glu Ser Asn Leu Gln
145                 150                 155                 160

Asn Val Val Ala Glu Thr Met Ser Gln Gln Gln Arg Ser Val Ser
                165                 170                 175

<210> SEQ ID NO 3
<211> LENGTH: 342
<212> TYPE: DNA
<213> ORGANISM: Anaplasma phagocytophilum
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (230)..(232)
<223> OTHER INFORMATION: n is a, c, g, or t

<400> SEQUENCE: 3
ttatgcgcta cagtgcacca catctatcaa ggaaattacg aagatcgcaa caacgacaaa      60
ggtagctccc gtggcggcgg tactacatat tatccaatga caatgtctgc aagtgcttct     120
gaagagtccc ttagcagcat aatatctgaa ggagntttga gtaagacatc gctaccaagt     180
tactccgcag ccactgctac aggtactgga aatgnaactg gtgaggtttn nncacattct     240
cattcatctg gtaaaagtag cagcaaacca gaatctcgcc ctgagagcaa tctacagaat     300
gtggtagcag aaaccatgtc gcagcaacaa aggagcgtct cc                        342

<210> SEQ ID NO 4
<211> LENGTH: 525
<212> TYPE: DNA
<213> ORGANISM: Anaplasma phagocytophilum
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (413)..(415)
<223> OTHER INFORMATION: n is a, c, g, or t

<400> SEQUENCE: 4
cacaaagggg tggattcaga tcggaagcat gatgcagaga aaacagaaga gaaaaaacat      60
ggtttgggta gcctctgcaa atcactcgcg ataaatctgg tctccttaat gggaacagcg     120
ctagttncca cacccataat actacttgca gtagttctat tagtgttggt gccagtatat     180
ctgttatgcg ctacagtgca ccacatctat caaggaaatt acgaagatcg caacaacgac     240
aaaggtagct cccgtggcgg cggtactaca tattatccaa tgacaatgtc tgcaagtgct     300
```

```
tctgaagagt ccccttagcag cataatatct gaaggagntt tgagtaagac atcgctacca    360
agttactccg cagccactgc tacaggtact ggaaatgnaa ctggtgaggt ttnnncacat    420
tctcattcat ctggtaaaag tagcagcaaa ccagaatctc gccctgagag caatctacag    480
aatgtggtag cagaaaccat gtcgcagcaa caaggagcg tctcc                     525
```

<210> SEQ ID NO 5
<211> LENGTH: 1065
<212> TYPE: DNA
<213> ORGANISM: Anaplasma phagocytophilum

<400> SEQUENCE: 5

```
ttgagtttta caatgtcgaa gttatcgctt gaccctactc agggctcaca tacagcagag     60
aatattgctt gttctatctt tgatatggta cttggtgtaa agtccactgc aaaactgtta   120
gcaggtacgt gggctggtac aagcagcact atttggaaga cagtaacagg agcagcttcc   180
tcaactaaag aagcgtcatc aaagtcgtat ggaaccctac gtagttcctt gggctcttcc   240
gcttctagaa ggatgctagg aacttgcgct accgccgctc tctgcttaac tgcacctttg   300
cttggcgcag ccgctgccgg agcggcaata acatgtgcct tgataaccat ttgcatggct   360
ttgctgttcc tcgtttttgta caccgtactc cacattgcct ctcagatgtt gcgttgtgca   420
tcgctactgt tgagcatggt atgcaatatc ctgcacagca cattccaccgc aactaagtct   480 tgcctcggag gtaagtcacc tgcgcgaaca actgaagagc gggtagctgg ggatttagat   540
cacaaagggg tggattcaga tcggaagcat gatgcagaga aaacagaaga gaaaaaacat   600
ggtttgggta gcctctgcaa atcactcgcg ataaatctgg tctccttaat gggaacagcg   660
ctagttacca cacccataat actacttgca gtagttctat tagtgttggt gccagtatat   720
ctgttatgcg ctacagtgca ccacatctat caaggaaatt acgaagatcg caacaacgac   780
aaaggtagct cccgtggcgg cggtactaca tattatccaa tgacaatgtc tgcaagtgct   840
tctgaagagt ccccttagcag cataatatct gaaggaggtt tgagtaagac atcgctacca   900
agttactccg cagccactgc tacaggtact ggaaatgcaa ctggtgaggt ttttcacat   960 tctcattcat ctggtaaaag tagcagcaaa ccagaatctc gccctgagag caatctacag  1020
aatgtggtag cagaaaccat gtcgcagcaa caaggagcg tctcc                    1065
```

<210> SEQ ID NO 6
<211> LENGTH: 355
<212> TYPE: PRT
<213> ORGANISM: Anaplasma phagocytophilum

<400> SEQUENCE: 6

```
Met Ser Phe Thr Met Ser Lys Leu Ser Leu Asp Pro Thr Gln Gly Ser
 1               5                  10                  15

His Thr Ala Glu Asn Ile Ala Cys Ser Ile Phe Asp Met Val Leu Gly
            20                  25                  30

Val Lys Ser Thr Ala Lys Leu Leu Ala Gly Thr Trp Ala Gly Thr Ser
        35                  40                  45

Ser Thr Ile Trp Lys Thr Val Thr Gly Ala Ala Ser Thr Lys Glu
    50                  55                  60

Ala Ser Ser Lys Ser Tyr Gly Thr Leu Arg Ser Ser Leu Gly Ser Ser
65                  70                  75                  80

Ala Ser Arg Arg Met Leu Gly Thr Cys Ala Thr Ala Ala Leu Cys Leu
                85                  90                  95

Thr Ala Pro Leu Leu Gly Ala Ala Ala Gly Ala Ala Ile Thr Cys
            100                 105                 110
```

Ala Leu Ile Thr Ile Cys Met Ala Leu Leu Phe Leu Val Leu Tyr Thr
            115                 120                 125

Val Leu His Ile Ala Ser Gln Met Leu Arg Cys Ala Ser Leu Leu Leu
        130                 135                 140

Ser Met Val Cys Asn Ile Leu His Ser Thr Phe Thr Ala Thr Lys Ser
145                 150                 155                 160

Cys Leu Gly Gly Lys Ser Pro Ala Arg Thr Thr Glu Glu Arg Val Ala
                165                 170                 175

Gly Asp Leu Asp His Lys Gly Val Asp Ser Asp Arg Lys His Asp Ala
            180                 185                 190

Glu Lys Thr Glu Glu Lys Lys His Gly Leu Gly Ser Leu Cys Lys Ser
        195                 200                 205

Leu Ala Ile Asn Leu Val Ser Leu Met Gly Thr Ala Leu Val Thr Thr
    210                 215                 220

Pro Ile Ile Leu Leu Ala Val Val Leu Leu Val Leu Val Pro Val Tyr
225                 230                 235                 240

Leu Leu Cys Ala Thr Val His His Ile Tyr Gln Gly Asn Tyr Glu Asp
                245                 250                 255

Arg Asn Asn Asp Lys Gly Ser Ser Arg Gly Gly Thr Thr Tyr Tyr
            260                 265                 270

Pro Met Thr Met Ser Ala Ser Ala Ser Glu Glu Ser Leu Ser Ser Ile
        275                 280                 285

Ile Ser Glu Gly Gly Leu Ser Lys Thr Ser Leu Pro Ser Tyr Ser Ala
    290                 295                 300

Ala Thr Ala Thr Gly Thr Gly Asn Ala Thr Gly Glu Val Phe Ser His
305                 310                 315                 320

Ser His Ser Ser Gly Lys Ser Ser Lys Pro Glu Ser Arg Pro Glu
                325                 330                 335

Ser Asn Leu Gln Asn Val Val Ala Glu Thr Met Ser Gln Gln Gln Arg
            340                 345                 350

Ser Val Ser
        355

<210> SEQ ID NO 7
<211> LENGTH: 585
<212> TYPE: DNA
<213> ORGANISM: Anaplasma phagocytophilum
<220> FEATURE:
<221> NAME/KEY: misc_feature
<222> LOCATION: (187)..(187)
<223> OTHER INFORMATION: N stands for G or A
<220> FEATURE:
<221> NAME/KEY: misc_feature
<222> LOCATION: (398)..(398)
<223> OTHER INFORMATION: N stands for A or G
<220> FEATURE:
<221> NAME/KEY: misc_feature
<222> LOCATION: (458)..(458)
<223> OTHER INFORMATION: N stands for A or C
<220> FEATURE:
<221> NAME/KEY: misc_feature
<222> LOCATION: (473)..(475)
<223> OTHER INFORMATION: N stands for T or no nucleic acid

<400> SEQUENCE: 7
tgcctcggag gtaagtcacc tgcgcgaaca actgaagagc gggtagctgg ggatttagat      60
cacaaagggg tggattcaga tcggaagcat gatgcagaga aaacagaaga gaaaaaacat     120
ggtttgggta gcctctgcaa atcactcgcg ataaatctgg tctccttaat gggaacagcg     180
ctagttncca cacccataat actacttgca gtagttctat tagtgttggt gccagtatat     240

```
ctgttatgcg ctacagtgca ccacatctat caaggaaatt acgaagatcg caacaacgac      300
aaaggtagct cccgtggcgg cggtactaca tattatccaa tgacaatgtc tgcaagtgct      360
tctgaagagt cccttagcag cataatatct gaaggagntt tgagtaagac atcgctacca      420
agttactccg cagccactgc tacaggtact ggaaatgnaa ctggtgaggt ttnnncacat      480
tctcattcat ctggtaaaag tagcagcaaa ccagaatctc gccctgagag caatctacag      540
aatgtggtag cagaaaccat gtcgcagcaa caaaggagcg tctcc                     585
```

<210> SEQ ID NO 8
<211> LENGTH: 195
<212> TYPE: PRT
<213> ORGANISM: Anaplasma phagocytophilum
<220> FEATURE:
<221> NAME/KEY: MISC_FEATURE
<222> LOCATION: (63)..(63)
<223> OTHER INFORMATION: X stands for A or T
<220> FEATURE:
<221> NAME/KEY: MISC_FEATURE
<222> LOCATION: (133)..(133)
<223> OTHER INFORMATION: X stands for D or G
<220> FEATURE:
<221> NAME/KEY: MISC_FEATURE
<222> LOCATION: (153)..(153)
<223> OTHER INFORMATION: X stands for A or E
<220> FEATURE:
<221> NAME/KEY: MISC_FEATURE
<222> LOCATION: (158)..(158)
<223> OTHER INFORMATION: X stands for F or no amino acid

<400> SEQUENCE: 8

```
Cys Leu Gly Gly Lys Ser Pro Ala Arg Thr Thr Glu Glu Arg Val Ala
1               5                   10                  15

Gly Asp Leu Asp His Lys Gly Val Asp Ser Asp Arg Lys His Asp Ala
            20                  25                  30

Glu Lys Thr Glu Glu Lys Lys His Gly Leu Gly Ser Leu Cys Lys Ser
        35                  40                  45

Leu Ala Ile Asn Leu Val Ser Leu Met Gly Thr Ala Leu Val Xaa Thr
    50                  55                  60

Pro Ile Ile Leu Leu Ala Val Val Leu Leu Val Leu Pro Val Tyr
65                  70                  75                  80

Leu Leu Cys Ala Thr Val His His Ile Tyr Gln Gly Asn Tyr Glu Asp
                85                  90                  95

Arg Asn Asn Asp Lys Gly Ser Ser Arg Gly Gly Gly Thr Thr Tyr Tyr
            100                 105                 110

Pro Met Thr Met Ser Ala Ser Ala Ser Glu Glu Ser Leu Ser Ser Ile
        115                 120                 125

Ile Ser Glu Gly Xaa Leu Ser Lys Thr Ser Leu Pro Ser Tyr Ser Ala
    130                 135                 140

Ala Thr Ala Thr Gly Thr Gly Asn Xaa Thr Gly Glu Val Xaa Ser His
145                 150                 155                 160

Ser His Ser Ser Gly Lys Ser Ser Lys Pro Glu Ser Arg Pro Glu
                165                 170                 175

Ser Asn Leu Gln Asn Val Val Ala Glu Thr Met Ser Gln Gln Gln Arg
            180                 185                 190

Ser Val Ser
        195
```

<210> SEQ ID NO 9
<211> LENGTH: 43
<212> TYPE: PRT

<213> ORGANISM: Anaplasma phagocytophilum

<400> SEQUENCE: 9

Cys Ala Thr Val His His Ile Tyr Gln Gly Asn Tyr Glu Asp Arg Asn
1               5                   10                  15

Asn Asp Lys Gly Ser Ser Arg Gly Gly Gly Thr Thr Tyr Pro Met
            20                  25                  30

Thr Met Ser Ala Ser Ala Ser Glu Glu Ser Leu
        35                  40

<210> SEQ ID NO 10
<211> LENGTH: 40
<212> TYPE: PRT
<213> ORGANISM: Anaplasma phagocytophilum

<400> SEQUENCE: 10

Cys Leu Gly Gly Lys Ser Pro Ala Arg Thr Thr Glu Glu Arg Val Ala
1               5                   10                  15

Gly Asp Leu Asp His Lys Gly Val Asp Ser Asp Arg Lys His Asp Ala
            20                  25                  30

Glu Lys Thr Glu Glu Lys Lys His
        35                  40

<210> SEQ ID NO 11
<211> LENGTH: 35
<212> TYPE: PRT
<213> ORGANISM: Anaplasma phagocytophilum
<220> FEATURE:
<221> NAME/KEY: MISC_FEATURE
<222> LOCATION: (1)..(1)
<223> OTHER INFORMATION: X stands for C or no amino acid
<220> FEATURE:
<221> NAME/KEY: MISC_FEATURE
<222> LOCATION: (2)..(2)
<223> OTHER INFORMATION: X stands for A or E
<220> FEATURE:
<221> NAME/KEY: MISC_FEATURE
<222> LOCATION: (7)..(7)
<223> OTHER INFORMATION: X stands for F or no amino acid

<400> SEQUENCE: 11

Xaa Xaa Thr Gly Glu Val Xaa Ser His Ser His Ser Ser Gly Lys Ser
1               5                   10                  15

Ser Ser Lys Pro Glu Ser Arg Pro Glu Ser Asn Leu Gln Asn Val Val
            20                  25                  30

Ala Glu Thr
        35

<210> SEQ ID NO 12
<211> LENGTH: 355
<212> TYPE: PRT
<213> ORGANISM: Anaplasma phagocytophilum
<220> FEATURE:
<221> NAME/KEY: MISC_FEATURE
<222> LOCATION: (223)..(223)
<223> OTHER INFORMATION: X stands for A or T
<220> FEATURE:
<221> NAME/KEY: MISC_FEATURE
<222> LOCATION: (293)..(293)
<223> OTHER INFORMATION: X stands for D or G
<220> FEATURE:
<221> NAME/KEY: MISC_FEATURE
<222> LOCATION: (313)..(313)
<223> OTHER INFORMATION: X stands for E or A
<220> FEATURE:
<221> NAME/KEY: MISC_FEATURE
<222> LOCATION: (318)..(318)
<223> OTHER INFORMATION: X stands for F or no amino acid -continued

```
<400> SEQUENCE: 12

Met Ser Phe Thr Met Ser Lys Leu Ser Leu Asp Pro Thr Gln Gly Ser
1               5                   10                  15

His Thr Ala Glu Asn Ile Ala Cys Ser Ile Phe Asp Met Val Leu Gly
            20                  25                  30

Val Lys Ser Thr Ala Lys Leu Leu Ala Gly Thr Trp Ala Gly Thr Ser
        35                  40                  45

Ser Thr Ile Trp Lys Thr Val Thr Gly Ala Ala Ser Ser Thr Lys Glu
    50                  55                  60

Ala Ser Ser Lys Ser Tyr Gly Thr Leu Arg Ser Ser Leu Gly Ser Ser
65                  70                  75                  80

Ala Ser Arg Arg Met Leu Gly Thr Cys Ala Thr Ala Ala Leu Cys Leu
                85                  90                  95

Thr Ala Pro Leu Leu Gly Ala Ala Ala Gly Ala Ala Ile Thr Cys
                100                 105                 110

Ala Leu Ile Thr Ile Cys Met Ala Leu Leu Phe Leu Val Leu Tyr Thr
            115                 120                 125

Val Leu His Ile Ala Ser Gln Met Leu Arg Cys Ala Ser Leu Leu Leu
        130                 135                 140

Ser Met Val Cys Asn Ile Leu His Ser Thr Phe Thr Ala Thr Lys Ser
145                 150                 155                 160

Cys Leu Gly Gly Lys Ser Pro Ala Arg Thr Thr Glu Glu Arg Val Ala
                165                 170                 175

Gly Asp Leu Asp His Lys Gly Val Asp Ser Asp Arg Lys His Asp Ala
                180                 185                 190

Glu Lys Thr Glu Glu Lys Lys His Gly Leu Gly Ser Leu Cys Lys Ser
            195                 200                 205

Leu Ala Ile Asn Leu Val Ser Leu Met Gly Thr Ala Leu Val Xaa Thr
    210                 215                 220

Pro Ile Ile Leu Leu Ala Val Val Leu Leu Val Leu Val Pro Val Tyr
225                 230                 235                 240

Leu Leu Cys Ala Thr Val His His Ile Tyr Gln Gly Asn Tyr Glu Asp
                245                 250                 255

Arg Asn Asn Asp Lys Gly Ser Ser Arg Gly Gly Gly Thr Thr Tyr Tyr
                260                 265                 270

Pro Met Thr Met Ser Ala Ser Ala Ser Glu Glu Ser Leu Ser Ser Ile
            275                 280                 285

Ile Ser Glu Gly Xaa Leu Ser Lys Thr Ser Leu Pro Ser Tyr Ser Ala
    290                 295                 300

Ala Thr Ala Thr Gly Thr Gly Asn Xaa Thr Gly Glu Val Xaa Ser His
305                 310                 315                 320

Ser His Ser Ser Gly Lys Ser Ser Lys Pro Glu Ser Arg Pro Glu
                325                 330                 335

Ser Asn Leu Gln Asn Val Val Ala Glu Thr Met Ser Gln Gln Gln Arg
            340                 345                 350

Ser Val Ser
        355
```

ANAPLASMA PHAGOCYTOPHILUM (APH) ANTIGENS AND ANTIBODIES SPECIFIC FOR ANAPLASMA

PRIORITY

This application is a national stage entry of International Application No. PCT/US2008/084391, filed on Nov. 21, 2008, which claims the benefit of the filing date of U.S. Provisional Application Ser. No. 60/990,420, filed Nov. 27, 2007. The entire contents of the foregoing applications are incorporated by reference herein in their entirety.

SEQUENCE LISTING

This document incorporates by reference herein an electronic sequence listing text file, which is filed in electronic format via EFS-Web. The text file is named "07-060-WO.ST25.txt," is 18,182 bytes, and was created on May 27, 2010.

BACKGROUND OF THE INVENTION

Anaplasmosis occurs in numerous mammal species such as humans, horses, dogs, cats deer, and ruminants and is caused by infection of granulocytic cells with the tick-borne agent *Anaplasma phagocytophilum* ("Aph") (formerly known as *Ehrlichia equi*). Frequently reported clinical signs in granulocytic ehrlichiosis in humans are leukopenia and thrombocytopenia. Common clinical signs in dogs are fever, thrombocytopenia, swelling of the lymph nodes, and anexoria.

*Anaplasma platys* ("Apl") (formerly known as *Ehrlichia platys*) is another agent that is likely transmitted through ticks such as *Rhipicephalus sanguineus* or other arthropod. *A. platys* may be co-transmitted by a tick with *Ehrlichia canis*. *A. platys* can cause infectious canine cyclic thrombocytopenia (ICCT), but infected dogs are usually asymptomatic. *A. platys* infection is difficult to detect in vivo because the numbers of the bacteria in the blood are usually low. Serologic tests for Apl can be inaccurate because of cross-reactivity with other *Anaplasma* sp.

Tickborne infectious disease caused by *A. phagocytophilum* in human and dogs is a serious problem, whereas *A. platys* infection is presently considered to be of minor importance. Current serodiagnostic tools for *A. phagocytophilum* can not differentiate the two infections. Methods of detecting Aph and Apl and methods of differentiating between the two infections are needed in the art.

The onset of clinical symptoms occurs during the acute phase of anaplasmosis—typically within 7 to 14 days post infection—and can precede the advent of measurable levels of antibodies against some Aph antigens. Thus, there is a need for a rapid, sensitive and reliable immunological test for Aph infection in mammals exhibiting clinical symptoms of acute anaplasmosis.

SUMMARY OF THE INVENTION

One embodiment of the invention provides a purified polypeptide that is at least 95% identical to SEQ ID NO:1, 2, 6, 8, 9, 10, 11, or 12, wherein the purified polypeptide consists of less than about 300, 150, 100, or 50 contiguous naturally occurring *Anaplasma phagocytophilum* amino acids. The polypeptide can specifically binds an antibody specific for *Anaplasma phagocytophilum*. The purified polypeptide can be linked to an indicator reagent, an amino acid spacer, an amino acid linker, a signal sequence, a stop transfer sequence, a transmembrane domain, a protein purification ligand, a heterologous polypeptide, one or more additional polypeptides comprising SEQ ID NO:1, 2, 6, 8, 9, 10, 11, 12 or a combination thereof. The invention provides isolated polynucleotides that encode the purified polypeptides of the invention.

Another embodiment of the invention provides a method of detecting antibodies that specifically bind an *Anaplasma phagocytophilum* polypeptide in a test sample. The method comprises contacting one or more purified polypeptides at least 95% identical to SEQ ID NO:1, 9 or 11, with the test sample, under conditions that allow polypeptide/antibody complexes to form. The purified polypeptides can consist of less than about 150 contiguous naturally occurring *Anaplasma phagocytophilum* amino acids. The polypeptide/antibody complexes are detected. The detection of the polypeptide/antibody complexes is an indication that antibodies specific for *Anaplasma phagocytophilum* are present in the test sample, and the lack of detection of the polypeptide/antibody complexes is an indication that antibodies specific for *Anaplasma phagocytophilum* are not present in the test sample. The complexes can be contacted with an indicator reagent prior to the detection step. The amount of antibodies in the test sample can be determined. The one or more purified polypeptides can be attached to a substrate. The one or more purified polypeptides can be linked to an indicator reagent, an amino acid spacer, an amino acid linker, a signal sequence, a stop transfer sequence, a transmembrane domain, a protein purification ligand, a heterologous protein, one or more additional polypeptides comprising SEQ ID NO:1, 9, or 11, or a combination thereof.

Even another embodiment of the invention provides a method of detecting an *Anaplasma phagocytophilum* infection in a subject. The method comprises obtaining a biological sample from the subject; contacting one or more purified polypeptides that are at least 95% identical to SEQ ID NO:1, 9 or 11, wherein the purified polypeptides consist of less than about 150 contiguous naturally occurring *Anaplasma phagocytophilum* amino acids, with the biological sample under conditions that allow polypeptide/antibody complexes to form; and detecting the polypeptide/antibody complexes. The detection of the polypeptide/antibody complexes is an indication that the subject has an *Anaplasma phagocytophilum* infection and the lack of detection of the polypeptide/antibody complexes is an indication that the subject does not have an *Anaplasma phagocytophilum* infection.

Still another embodiment of the invention provides an antibody that specifically binds to a polypeptide consisting of SEQ ID NO:1, 2, 6, 8, 9, 10, 11, or 12. The antibody can be a monoclonal antibody, polyclonal antibody, a Fab fragment, a Fab' fragment, Fab'-SH fragment, F(ab')$_2$ fragment, Fv fragment, or a single chain antibody.

Yet another embodiment of the invention provides a method of detecting an *Anaplasma phagocytophilum* polypeptide in a sample. The method comprises contacting one or more antibodies that specifically bind to a polypeptide consisting of SEQ ID NO:1, 9, or 11 with the sample under conditions that allow polypeptide/antibody complexes to form, and detecting the polypeptide/antibody complexes. The detection of the polypeptide/antibody complexes is an indication that an *Anaplasma phagocytophilum* polypeptide is present in the sample and the lack of detection of the polypeptide/antibody complexes is an indication that an *Anaplasma phagocytophilum* polypeptide is not present in the sample. The one or more antibodies can be monoclonal antibodies, polyclonal antibodies, Fab fragments, Fab' fragments, Fab'-SH fragments, F(ab')$_2$ fragments, Fv fragments, or single chain antibodies.

Even another embodiment of the invention provides a method of detecting antibodies that specifically bind an *Anaplasma platys* polypeptide, an *Anaplasma phagocytophilum* polypeptide or both an *Anaplasma platys* polypeptide and an *Anaplasma phagocytophilum* polypeptide. The method comprises contacting one or more purified polypeptides that are at least 95% identical to SEQ ID NO:2, 6, 8, 10, or 12 with a test sample, under conditions that allow polypeptide/antibody complexes to form, and detecting the polypeptide/antibody complexes. The detection of the polypeptide/antibody complexes is an indication that antibodies specific for *Anaplasma platys* and/or *Anaplasma phagocytophilum* are present in the test sample, and the lack of detection of the polypeptide/antibody complexes is an indication that antibodies specific for *Anaplasma platys* and/or *Anaplasma phagocytophilum* are not present in the test sample. The amount of antibodies in the test sample can be determined. The one or more purified polypeptides can be attached to a substrate. The one or more purified polypeptides can be linked to an indicator reagent, an amino acid spacer, an amino acid linker, a signal sequence, a stop transfer sequence, a transmembrane domain, a protein purification ligand, a heterologous protein, one or more additional polypeptides comprising SEQ ID NO:1, 2, 6, 8, 9, 10, 11, 12 or a combination thereof.

Another embodiment of the invention provides a method of detecting an *Anaplasma phagocytophilum* and/or *Anaplasma platys* infection in a subject. The method comprises obtaining a biological sample from the subject; contacting one or more purified polypeptides comprising SEQ ID NO:2, 6, 8, 10, or 12 with the biological sample under conditions that allow polypeptide/antibody complexes to form; and detecting the polypeptide/antibody complexes. The detection of the polypeptide/antibody complexes is an indication that the subject has an *Anaplasma phagocytophilum* and/or *Anaplasma platys* infection and the lack of detection of polypeptide/antibody complexes is an indication that the subject does not have an *Anaplasma phagocytophilum* and/or *Anaplasma platys* infection.

Even another embodiment of the invention provides a method of detecting an *Anaplasma phagocytophilum* polypeptide, an *Anaplasma platys* polypeptide, or an *Anaplasma phagocytophilum* polypeptide and an *Anaplasma platys* polypeptide, in a sample. The method comprises contacting one or more antibodies that specifically bind to a polypeptide consisting of SEQ ID NO:2, 6, 8, 10, or 12 with the sample under conditions that allow polypeptide/antibody complexes to form, and detecting the polypeptide/antibody complexes. The detection of the polypeptide/antibody complexes is an indication that an *Anaplasma phagocytophilum* polypeptide, an *Anaplasma platys* polypeptide, or an *Anaplasma phagocytophilum* polypeptide and an *Anaplasma platys* polypeptide is present in the sample and the lack of detection of the polypeptide/antibody complexes is an indication that an *Anaplasma phagocytophilum* and an *Anaplasma platys* polypeptide is not present in the sample.

Still another embodiment of the invention provides a method of detecting *Anaplasma platys* polypeptides and *Anaplasma phagocytophilum* polypeptides in a sample. The method comprises:
  (a) contacting one or more antibodies that specifically bind to a polypeptide consisting of SEQ ID NO:2, 6, 8, 10, or 12 with the sample under conditions that allow polypeptide/antibody complexes to form and detecting the polypeptide/antibody complexes; and
  (b) contacting one or more antibodies that specifically bind to a polypeptide consisting of SEQ ID NO:1, 9, or 11 with the sample under conditions that allow polypeptide/antibody complexes to form and detecting the polypeptide/antibody complexes;
  (c) wherein if the polypeptide/antibody complexes are detected in step (a) and in step (b) then the sample contains *Anaplasma phagocytophilum* polypeptides and may also contain *Anaplasma platys* polypeptides; wherein if the polypeptide/antibody complexes are detected in step (a) and are not detected in step (b) then the sample contains *Anaplasma platys* polypeptides and does not contain *Anaplasma phagocytophilum* polypeptides; wherein if the polypeptide complexes are not detected in step (a) and are not detected in step (b) then the sample does not contain *Anaplasma platys* polypeptides and does not contain *Anaplasma phagocytophilum* polypeptides.

Another embodiment of the invention provides a method of detecting antibodies that specifically bind an *Anaplasma platys* polypeptide, an *Anaplasma phagocytophilum* polypeptide, or both an *Anaplasma platys* polypeptide and an *Anaplasma phagocytophilum* polypeptide. The method comprises:
  (a) contacting one or more purified polypeptides that are at least 95% identical to SEQ ID NO:2, 6, 8, 10, or 12 with a test sample, under conditions that allow polypeptide/antibody complexes to form and detecting the polypeptide/antibody complexes;
  (b) contacting one or more purified polypeptides that are at least 95% identical to SEQ ID NO:1, 9, or 11, wherein the purified polypeptide consists of less than about 150 contiguous naturally occurring *Anaplasma phagocytophilum* amino acids, with a test sample, under conditions that allow polypeptide/antibody complexes to form and detecting the polypeptide/antibody complexes. If the polypeptide/antibody complexes are detected in step (a) and in step (b) then the sample contains antibodies the specifically bind *Anaplasma phagocytophilum* polypeptides and *Anaplasma platys* polypeptides and antibodies that specifically bind only *Anaplasma platys* polypeptides; wherein if the polypeptide/antibody complexes are detected in step (a) and are not detected in step (b) then the sample contains antibodies that specifically bind *Anaplasma platys* polypeptides and *Anaplasma phagocytophilum* polypeptides and does not contain antibodies that specifically bind only *Anaplasma phagocytophilum* polypeptides; wherein if the polypeptide complexes are not detected in step (a) and are not detected in step (b) then the sample does not contain antibodies specific for *Anaplasma platys* polypeptides and does not contain antibodies specific for *Anaplasma phagocytophilum* polypeptides.

Even another embodiment of the invention provides a composition comprising a purified polypeptide of the invention and a pharmaceutically-acceptable or veterinarily acceptable carrier. The composition can further comprise an adjuvant.

Still another embodiment of the invention provides an immunogen comprising a polypeptide having at least 95% identity to SEQ ID NO:1, 2, 6, 8, 9, 10, 11, or 12, and one or more additional regions or moieties covalently joined to the polypeptide at the carboxyl terminus or amino terminus, wherein each region or moiety has at least one of the following properties: enhances the immune response, facilitates purification, or facilitates polypeptide stability.

Yet another embodiment of the invention provides a method of treating or ameliorating *Anaplasma platys* infection, *Anaplasma phagocytophilum* infection, or both in a mammalian subject. The method comprises administering to the mammalian subject a therapeutically effective amount of a composition comprising a purified polypeptide of the invention and a pharmaceutically-acceptable or veterinarily acceptable carrier. The composition can further comprise an adjuvant.

Another embodiment of the invention provides a method of inducing an immune response in a mammal comprising administering to the mammal an immunologically effective amount of a composition comprising a purified polypeptide of the invention and a pharmaceutically-acceptable or veterinarily acceptable carrier. The composition can further comprise an adjuvant.

Still another embodiment of the invention provides a first purified polypeptide that specifically binds an antibody, wherein the antibody specifically binds a second purified polypeptide, wherein the second purified polypeptide consists of SEQ ID NO:1, 2, 6, 8, 9, 10, 11, or 12. The first purified polypeptide can consist of at least 10, but less than 300 contiguous amino acids of SEQ ID NO: 1, 2, 6, 8, 9, 10, 11 or 12. The first purified polypeptide can be at least 95% identical to SEQ ID NO: 1, 2, 6, 8, 9, 10, 11 or 12. The first purified polypeptide can be linked to an indicator reagent, an amino acid spacer, an amino acid linker, a signal sequence, a stop transfer sequence, a transmembrane domain, a protein purification ligand, a heterologous polypeptide, one or more additional polypeptides comprising SEQ ID NO:1, 2, 6, 8, 9, 10, 11, 12, or a combination thereof.

The invention therefore provides methods and compositions for the detection and treatment of Apl and/or Aph infection.

DETAILED DESCRIPTION OF THE INVENTION

*Anaplasma phagocytophilum* Polypeptides

The singular forms "a," "an", and "the" used herein include plural referents unless the context clearly dictates otherwise.

A polypeptide is a polymer of two or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, etc, or combinations thereof. A polypeptide preparation that is substantially free of cellular material, culture medium, chemical precursors, chemicals used in synthesis of the polypeptide, etc. has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

The term "polypeptides" can refer to one or more of one type of polypeptide (a set of polypeptides). "Polypeptides" can also refer to mixtures of two or more different types of polypeptides (a mixture of polypeptides). The terms "polypeptides" or "polypeptide" can each also mean "one or more polypeptides."

One embodiment of the invention provides an Aph polypeptide as shown in SEQ ID NO: 1, SEQ ID NO:2, SEQ ID NO:8, SEQ ID NO:9, SEQ ID NO:10 or SEQ ID NO:11.

```
                                          SEQ ID NO: 1
(clone14)
LCATVHHIYQ GNYEDRNNDK GSSRGGGTTY YPMTMSASAS

EESLSSIISE GXLSKTSLPS YSAATATGTG NXTGEVXSHS

HSSGKSSSKP ESRPESNLQN VVAETMSQQQ RSVS
```

Wherein the X at position 52 is D or G; the X at position 72 is E or A; and the X at position 77 is absent or is F.

```
                                          SEQ ID NO: 2
(clone13)
HKGVDSDRKH DAEKTEEKKH GLGSLCKSLA INLVSLMGTA

LVXTPIILLA VVLLVLVPVY LLCATVHHIY QGNYEDRNND

KGSSRGGGTT YYPMTMSASA SEESLSSIIS EGXLSKTSLP

SYSAATATGT GNXTGEVXSH SHSSGKSSSK PESRPESNLQ

NVVAETMSQQ QRSVS
```

Wherein the X at position 43 is A or T; wherein the X at position 113 is D or G; wherein the X at position 133 is A or E; and wherein the X at position 138 is F or absent.

```
                                          SEQ ID NO: 8
(clone13ext)
CLGGKSPART TEERVAGDLD HKGVDSDRKH DAEKTEEKKH

GLGSLCKSLA INLVSLMGTA LVXTPIILLA VVLLVLVPVY

LLCATVHHIY QGNYEDRNND KGSSRGGGTT YYPMTMSASA

SEESLSSIIS EGXLSKTSLP SYSAATATGT GNXTGEVXSH

SHSSGKSSSK PESRPESNLQ NVVAETMSQQ QRSVS
```

Wherein the X at position 63 is A or T; wherein the X at position 133 is D or G; wherein the X at position 153 is A or E; and wherein the X at position 158 is F or absent.

```
                                          SEQ ID NO: 9
(p37-1)
CATVHHIYQG NYEDRNNDKG SSRGGGTTYY PMTMSASASE ESL
```

```
                                          SEQ ID NO: 10
(p37-2)
CLGGKSPART TEERVAGDLD HKGVDSDRKH DAEKTEEKKH G
```

```
                                          SEQ ID NO: 11
(p37-3)
XXTGEVXSHS HSSGKSSSKP ESRPESNLQN VVAET
```

Wherein the X at position 1 is C or absent; wherein the X at position 2 is A or E; and wherein the X at position 7 is F or absent.

One embodiment of the invention provides a purified polypeptide comprising SEQ ID NOs:1, 9 or 11 wherein the polypeptide consists of less than about 150, 140, 130, 120, 110, 90, 80, 70, 60, 50, 40, 35, 30, 25 or 20 (or any range between 150 and 20) contiguous naturally occurring *Anaplasma phagocytophilum* amino acids. Another embodiment of the invention provides a purified polypeptide comprising SEQ ID NOs:1, 9 or 11 wherein the polypeptide consists of more than about 20, 25, 30, 35, 40, 50, 60, 70, 80, 90, 110, 120, 130, 140, or 150 (or any range between 20 and 150) contiguous naturally occurring *Anaplasma phagocytophilum* amino acids. Naturally occurring Aph amino acids are any polypeptides naturally produced by an Aph organism. That is, a purified polypeptide contains a polypeptide shown in SEQ ID NO:1, 9, or 11, but contains less than about 150, 140, 130, 120, 110, 90, 80, 70, 60, 50, 40, 35, 30, 25 or 20 contiguous naturally occurring *Anaplasma phagocytophilum* amino acids. That is, the purified polypeptide is smaller than the full length polypeptide. The purified polypeptide can comprise additional heterologous amino acids (that is, amino acids that are not from Aph) and even additional Aph amino acids as long as they do not naturally occur contiguously with SEQ ID NOs:1, 2, 8, 9, 10, or 11. Another embodiment provides a purified polypeptide comprising SEQ ID NO:2, 6, 8, 10, or 12 wherein the polypeptide consists of less than about 350, 300, 275, 250, 225, 200, 195, 175, 150, 125, 100, 75, 50, 45, 40, 35, 30, or 25 (or any range between 350 and 25) contiguous naturally occurring *Anaplasma phagocytophilum* amino acids. That is, the purified polypeptide is smaller than the full length polypeptide (SEQ ID NO:6). Another embodiment provides a purified polypeptide comprising SEQ ID NO:2, 6, 8, 10, or 12 wherein the polypeptide consists of more than about 25, 30, 35, 40, 45, 50, 75, 100, 125, 150, 175, 195, 200, 225, 250, 275, 300 or 350 (or any range between 25 and 350) contiguous naturally occurring *Anaplasma phagocytophilum* amino acids.

In one embodiment of the invention, a purified polypeptide can comprise SEQ ID NO:9, SEQ ID NO:10 or SEQ ID NO:11, wherein the polypeptide consists of more than about 200, 175, 150, 160, 150, 140, 130, 120, 114, 110, 100, 90, 80, 70, 60, 50, 43, 40, 35, 30, or 25 (or any range between 200 and 25) contiguous naturally occurring *Anaplasma phagocytophilum* amino acids. Another embodiment provides a purified polypeptide comprising SEQ ID NO:9, SEQ ID NO:10 or SEQ ID NO:11, wherein the polypeptide consists of less than about 200, 175, 150, 160, 150, 140, 130, 120, 114, 110, 100, 90, 80, 70, 60, 50, 43, 40, 35, 30, or 25 (or any range between 200 and 25) contiguous naturally occurring *Anaplasma phagocytophilum* amino acids. The fact that these polypeptides are smaller than the full length Aph polypeptide APH 0915 (GenBank Accession Number ABD43857) (SEQ ID NO:6) is important because smaller polypeptides can have greater specificity and/or sensitivity than full length polypeptides in Apl and/or Aph assays. Additionally, these smaller polypeptides can be less expensive to manufacture, and may be obtained at greater purity, than the full length polypeptide.

```
                                                    SEQ ID NO: 6
(APH_0915 hypothetical protein {Anaplasma phago-
cytophilum HZ})
MSFTMSKLSLDPTQGSHTAENIACSIFDMVLGVKSTAKLLAGTWAGTSST

IWKTVTGAASSTKEASSKSYGTLRSSLGSSASRRMLGTCATAALCLTAPL

LGAAAAGAAITCALITICMALLFLVLYTVLHIASQMLRCASLLLSMVCNI

LHSTFTATKSCLGGKSPARTTEERVAGDLDHKGVDSDRKHDAEKTEEKKH

GLGSLCKSLAINLVSLMGTALVTTPIILLAVVLLVLVPVYLLCATVHHIY

QGNYEDRNNDKGSSRGGGTTYYPMTMSASASEESLSSIISEGGLSKTSLP

SYSAATATGTGNATGEVFSHSHSSGKSSSKPESRPESNLQNVVAETMSQQ

QRSVS
```

Another embodiment of the invention provides a polypeptide shown in SEQ ID NO:12:

```
                                                    SEQ ID NO: 12
MSFTMSKLSL DPTQGSHTAE NIACSIFDMV LGVKSTAKLL AGTWAGTSST IWKTVTGAAS  60

STKEASSKSY GTLRSSLGSS ASRRMLGTCA TAALCLTAPL LGAAAAGAAI TCALITICMA 120

LLFLVLYTVL HIASQMLRCA SLLLSMVCNI LHSTFTATKS CLGGKSPART TEERVAGDLD 180

HKGVDSDRKH DAEKTEEKKH GLGSLCKSLA INLVSLMGTA LVXTPIILLA VVLLVLVPVY 240

LLCATVHHIY QGNYEDRNND KGSSRGGGTT YYPMTMSASA SEESLSSIIS EGXLSKTSLP 300

SYSAATATGT GNXTGEVXSH SHSSGKSSSK PESRPESNLQ NVVAETMSQQ QRSVS
``` wherein the X at position 223 is A or T, the X at position 293 is D or G, the X at position 313 is E or A and the X at position 318 is F or absent.

One embodiment of the invention provides a purified polypeptide that is less than about 360, 350, 300, 250, 200, 175, 150, 125, 100, 90, 80, 70, 60, 50, 40, 35, 30, 25, 20, or 10 contiguous naturally Aph amino acids and greater than about 10, 20, 25, 30, 35, 40, 50, 60, 70, 80, 90, 100, 125, 150, 175, 200, 250, 300, 350, or 360 contiguous amino acids of SEQ ID NOs:1-2, 6, and 8-10 (or any range between 360 and 10 amino acids).

One embodiment of the invention provides a purified polypeptide comprising at least about 10, 20, 25, 30, 35, 40, 50, 60, 70, 80, 90, 100, 125, 150, 175, 200, 225, 250, 275, 300, 325, 350, 360 or more contiguous amino acids of SEQ ID NOs:1-2, 6, and 8-12. Therefore, a polypeptide of the invention can be, for example, about 19 to about 40; about 19 to about 50; about 19 to about 100; or about 19 to about 150 amino acids in length.

Variant polypeptides are at least about 79% or 80%, or about 81, 82, 83, 84, 85, 86, 87, 88, 89, 90, 91, 92, 93, 94, 95, 96, 97, 98, or 99% identical to the polypeptide sequences shown in SEQ ID NOs:1-2, 6, and 8-12 and are also polypeptides of the invention. For example, a variant polypeptide of SEQ ID NO:11 can be about at least 97% (about 1 amino acid change), 94% (about 2 amino acid changes), 91% (about 3 amino acid changes), 89% (about 4 amino acid changes), 86% (about 5 amino acid changes), identical to SEQ ID NO:11.

One embodiment of the invention provides a purified polypeptide that is less than 150 contiguous amino acids and greater than about 10, 20, 30, 35, 40, 50, 60, 70, 80, 90, 100, 110, 120, 130 or 140 contiguous amino acids of SEQ ID NO:6 (or SEQ ID NO:6 having an A at position 223, a D at position 293, an E at position 313, and no amino acid at position 318). For example, a purified polypeptide of the invention is less than about 150 contiguous amino acids of SEQ ID NO:6 (or SEQ ID NO:6 having an A at position 223, a D at position 293, an E at position 313, and no amino acid at position 318) and greater than about 30 contiguous amino acids of SEQ ID NO:6 (or SEQ ID NO:6 having an A at position 223, a D at position 293, an E at position 313, and no amino acid at position 318). Purified polypeptides of the invention can comprise, e.g., amino acids 150-355, 161-355, 181-355, 242-355 and fragments thereof of about greater than 10, 20, 30, 35, 40, 50, 60, 70, 80, 90, 100, 110, 120, 130 or 140 contiguous amino acids of SEQ ID NO:6 (or SEQ ID NO:6 having an A at position 223, a D at position 293, an E at position 313, and no amino acid at position 318).

One embodiment of the invention provides a purified polypeptide comprising at least about 10, 20, 25, 30, 35, 40, 50, 60, 70, 80, 90, 100, 110, 120, 130, 140, 150, 160, 170, 190 or more contiguous amino acids of SEQ ID NOs:1, 2, 6, 8, 9, 10, 11, or 12.

Another embodiment of the invention provides a purified polypeptide comprising SEQ ID NO:1, 9, or 11, wherein the polypeptide consists of less than about 150 contiguous naturally occurring *Anaplasma phagocytophilum* amino acids or a purified polypeptide comprising SEQ ID NO: 2, 6, 8, 10, or 12, wherein the polypeptide consists of less than about 300 contiguous naturally occurring *Anaplasma phagocytophilum* amino acids.

Variant polypeptides at least about 80, or about 90, 91, 92, 93, 94, 95, 96, 98, or 99% identical to the polypeptide sequences shown in SEQ ID NOs:1, 2, 6, 8, 9, 10, 11, or 12 are also polypeptides of the invention. Variant polypeptides have one or more conservative amino acid variations or other minor modifications and retain biological activity, i.e., are biologically functional equivalents. A biologically active equivalent has substantially equivalent function when compared to the corresponding wild-type polypeptide. In one embodiment of the invention a polypeptide has 1, 2, 3, 4, 5, 10, 15, 20, 30, 40 or 50 conservative amino acid substitutions.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.,* 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variant polypeptides can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature, i.e., a heterologous amino acid sequence. A heterologous amino acid sequence can be from a non-*Anaplasma phagocytophilum* organism, a synthetic sequence, or an *Anaplasma phagocytophilum* sequence not usually located at the carboxy or amino terminus of a polypeptide of the invention. Additionally, a polypeptide can be covalently or non-covalently linked to compounds or molecules other than amino acids, such as indicator reagents. A polypeptide can be covalently or non-covalently linked to an amino acid spacer, an amino acid linker, a signal sequence, a stop transfer sequence, a transmembrane domain, a protein purification ligand, or a combination thereof. A polypeptide can also be linked to a moiety (i.e., a functional group that can be a polypeptide or other compound) that enhances an immune response (e.g., cytokines such as IL-2), a moiety that facilitates purification (e.g., affinity tags such as a six-histidine tag, trpE, glutathione, maltose binding protein), or a moiety that facilitates polypeptide stability (e.g., polyethylene glycol; amino terminus protecting groups such as acetyl, propyl, succinyl, benzyl, benzyloxycarbonyl or t-butyloxycarbonyl; carboxyl terminus protecting groups such as amide, methylamide, and ethylamide). In one embodiment of the invention a protein purification ligand can be one or more C amino acid residues at, for example, the amino terminus or carboxy terminus or both termini of a polypeptide of the invention. An amino acid spacer is a sequence of amino acids that are not associated with a polypeptide of the invention in nature. An amino acid spacer can comprise about 1, 5, 10, 20, 100, or 1,000 amino acids.

If desired, a polypeptide of the invention can be part of a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and Staphylococcal protein A, or combinations thereof. More than one polypeptide of the invention can be present in a fusion protein. A polypeptide of the invention can be operably linked to non-*Anaplasma phagocytophilum* proteins or *Anaplasma phagocytophilum* proteins to form fusion proteins. A fusion protein of the invention can comprise one or more of *Anaplasma phagocytophilum* polypeptides of the invention, fragments thereof, or combinations thereof. A fusion protein does not occur in nature. The term "operably linked" means that the polypeptide of the invention and the other polypeptides are fused in-frame to each other either to the N-terminus or C-terminus of the polypeptide of the invention.

Polypeptides of the invention can be in a multimeric form. That is, a polypeptide can comprise one or more copies of an *Anaplasma phagocytophilum* polypeptide of the invention or a combination thereof. A multimeric polypeptide can be a multiple antigen peptide (MAP). See e.g., Tam, J. Immunol. Methods, 196:17-32 (1996).

Polypeptides of the invention can comprise an antigen that is recognized by an antibody specific for *Anaplasma phagocytophilum*. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, CABIOS 4:181-186 (1988). For example, a polypeptide of the invention can be isolated and screened. A series of short peptides, which together span an entire polypeptide sequence, can be prepared by proteolytic cleavage. By starting with, for example, 100-mer polypeptide fragments (or smaller fragments), each fragment can be tested for the presence of epitopes recognized in an ELISA. For example, in an ELISA assay an *Anaplasma phagocytophilum* polypeptide, such as a 100-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from *Anaplasma phagocytophilum* cells.

An immunogenic polypeptide of the invention can comprise an amino acid sequence shown in SEQ ID NOs:1, 2, 6, 8, 9, 10, 11, 12 or fragments thereof. An immunogenic polypeptide can elicit antibodies or other immune responses (e.g., T-cell responses of the immune system) that recognize epitopes of a polypeptide having SEQ ID NOs:1, 2, 6, 8, 9, 10, 11, or 12. An immunogenic polypeptide of the invention can also be a fragment of a polypeptide that has an amino acid sequence shown in SEQ ID NOs:1, 2, 6, 8, 9, 10, 11, or 12. An immunogenic polypeptide fragment of the invention can be about 6, 10, 15, 20, 25, 30, 40, 50, 60, 70, 80, 90, 100, 150, 175, 200, 250, 300, 350 or more amino acids in length (or any range between 6 and 350). An immunogenic polypeptide of the invention can be about 350, 300, 250, 200, 175, 150, 125, 100, 90, 80, 70, 60, 50, 40, 30, 25, 20, 15, 10, 6, or less amino acids in length (or any range between 350 and 6).

*Anaplasma phagocytophilum* Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. A nucleic acid molecule existing among hundreds to millions of other nucleic acid molecules within, for example, cDNA or genomic libraries, or gel slices containing a genomic DNA restriction digest are not to be considered an isolated polynucleotide. The polynucleotides of the invention encode the polypeptides of the invention described above. In one embodiment of the invention the polynucleotides encode a polypeptide shown in SEQ ID NOs:1, 2, 6, 8, 9, 10, 11, 12 or fragments thereof. Examples of polynucleotides of the invention include: SEQ ID NOs 3, 4, 5, and 7.

```
                                          SEQ ID NO: 3
(clone14)
TTATGCGCTA CAGTGCACCA CATCTATCAA GGAAATTACG

AAGATCGCAA CAACGACAAA GGTAGCTCCC GTGGCGGCGG

TACTACATAT TATCCAATGA CAATGTCTGC AAGTGCTTCT

GAAGAGTCCC TTAGCAGCAT AATATCTGAA GGAGNTTTGA

GTAAGACATC GCTACCAAGT TACTCCGCAG CCACTGCTAC

AGGTACTGGA AATGNAACTG GTGAGGTTTN NNCACATTCT

CATTCATCTG GTAAAAGTAG CAGCAAACCA GAATCTCGCC

CTGAGAGCAA TCTACAGAAT GTGGTAGCAG AAACCATGTC

GCAGCAACAA AGGAGCGTCT CC
```

Wherein the N at position 155 is A or G; wherein the N at position 215 is A or C; and wherein the three N's at positions 230-232 are all T's or are all absent.

```
                                          SEQ ID NO: 4
(clone13)
CACAAAGGGG TGGATTCAGA TCGGAAGCAT GATGCAGAGA

AAACAGAAGA GAAAAAACAT GGTTTGGGTA GCCTCTGCAA

ATCACTCGCG ATAAATCTGG TCTCCTTAAT GGGAACAGCG

CTAGTTNCCA CACCCATAAT ACTACTTGCA GTAGTTCTAT

TAGTGTTGGT GCCAGTATAT CTGTTATGCG CTACAGTGCA

CCACATCTAT CAAGGAAATT ACGAAGATCG CAACAACGAC

AAAGGTAGCT CCCGTGGCGG CGGTACTACA TATTATCCAA

TGACAATGTC TGCAAGTGCT TCTGAAGAGT CCCTTAGCAG

CATAATATCT GAAGGAGNTT TGAGTAAGAC ATCGCTACCA

AGTTACTCCG CAGCCACTGC TACAGGTACT GGAAATGNAA

CTGGTGAGGT TTNNNCACAT TCTCATTCAT CTGGTAAAAG

TAGCAGCAAA CCAGAATCTC GCCCTGAGAG CAATCTACAG

AATGTGGTAG CAGAAACCAT GTCGCAGCAA CAAAGGAGCG TCTCC
```

Wherein the N at position 127 is G or A; wherein the N at position 338 is A or G; wherein the N at position 398 is A or C; wherein the three N's at positions 413-415 are all T's or are absent.

```
                                          SEQ ID NO: 5
(APH_0915 hypothetical gene {Anaplasma phagocyto-
philum HZ})
TTGAGTTTTACAATGTCGAAGTTATCGCTTGACCCTACTCAGGGCTCACA

TACAGCAGAGAATATTGCTTGTTCTATCTTTGATATGGTACTTGGTGTAA

AGTCCACTGCAAAACTGTTAGCAGGTACGTGGGCTGGTACAAGCAGCACT

ATTTGGAAGACAGTAACAGGAGCAGCTTCCTCAACTAAAGAAGCGTCATC

AAAGTCGTATGGAACCCTACGTAGTTCCTTGGGCTCTTCCGCTTCTAGAA

GGATGCTAGGAACTTGCGCTACCGCCGCTCTCTGCTTAACTGCACCTTTG

CTTGGCGCAGCCGCTGCCGGAGCGGCAATAACATGTGCCTTGATAACCAT

TTGCATGGCTTTGCTGTTCCTCGTTTTGTACACCGTACTCCACATTGCCT

CTCAGATGTTGCGTTGTGCATCGCTACTGTTGAGCATGGTATGCAATATC

CTGCACAGCACATTCACCGCAACTAAGTCTTGCCTCGGAGGTAAGTCACC

TGCGCGAACAACTGAAGAGCGGGTAGCTGGGGATTTAGATCACAAAGGGG

TGGATTCAGATCGGAAGCATGATGCAGAGAAAACAGAAGAGAAAAAACAT

GGTTTGGGTAGCCTCTGCAAATCACTCGCGATAAATCTGGTCTCCTTAAT

GGGAACAGCGCTAGTTACCACACCCATAATACTACTTGCAGTAGTTCTAT
```

-continued

```
TAGTGTTGGTGCCAGTATATCTGTTATGCGCTACAGTGCACCACATCTAT

CAAGGAAATTACGAAGATCGCAACAACGACAAAGGTAGCTCCCGTGGCGG

CGGTACTACATATTATCCAATGACAATGTCTGCAAGTGCTTCTGAAGAGT

CCCTTAGCAGCATAATATCTGAAGGAGGTTTGAGTAAGACATCGCTACCA

AGTTACTCCGCAGCCACTGCTACAGGTACTGGAAATGCAACTGGTGAGGT

TTTTTCACATTCTCATTCATCTGGTAAAAGTAGCAGCAAACCAGAATCTC

GCCCTGAGAGCAATCTACAGAATGTGGTAGCAGAAACCATGTCGCAGCAA

CAAAGGAGCGTCTCC
```

SEQ ID NO: 7
(clone 13ext)
```
TGCCTCGGAG GTAAGTCACC TGCGCGAACA ACTGAAGAGC

GGGTAGCTGG GGATTTAGAT CACAAAGGGG TGGATTCAGA

TCGGAAGCAT GATGCAGAGA AAACAGAAGA GAAAAAACAT

GGTTTGGGTA GCCTCTGCAA ATCACTCGCG ATAAATCTGG

TCTCCTTAAT GGGAACAGCG CTAGTTNCCA CACCCATAAT

ACTACTTGCA GTAGTTCTAT TAGTGTTGGT GCCAGTATAT

CTGTTATGCG CTACAGTGCA CCCACATCTAT CAAGGAAATT

ACGAAGATCG CAACAACGAC AAAGGTAGCT CCCGTGGCGG

CGGTACTACA TATTATCCAA TGACAATGTC TGCAAGTGCT

TCTGAAGAGT CCCTTAGCAG CATAATATCT GAAGGAGNTT

TGAGTAAGAC ATCGCTACCA AGTTACTCCG CAGCCACTGC

TACAGGTACT GGAAATGNAA CTGGTGAGGT TTNNNCACAT

TCTCATTCAT CTGGTAAAAG TAGCAGCAAA CCAGAATCTC

GCCCTGAGAG CAATCTACAG AATGTGGTAG CAGAAACCAT

GTCGCAGCAA CAAAGGAGCG TCTCC
```

Wherein the N at position 187 is G or A; wherein in the N at position 398 is A or G; wherein the N at position 458 is A or C; wherein the three N's at positions 473-475 are all T's or are all absent.

Polynucleotides of the invention can consist of less than about 900, 825, 750, 675, 600, 500, 450, 420, 390, 360, 330, 300, 225, 150, 120, or 90 (or any range between 900 and 90) contiguous, naturally occurring Aph polynucleotides. Polynucleotides of the invention can consist of greater than about 90, 120, 150, 225, 300, 330, 360, 390, 420, 450, 500, 600, 675, 750, 825, 900 or more (or any range between 90 and 900) contiguous, naturally occurring Aph polynucleotides. The purified polynucleotides can comprise additional heterologous nucleotides (that is, nucleotides that are not from Aph) and even additional Aph amino acids as long as they do not naturally occur contiguously with SEQ ID NOs:3, 4, 5, or 7. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A. One embodiment of the invention provides a purified polynucleotide comprising at least about 6, 10, 15, 20, 25, 30, 40, 50, 75, 100, 200, 300, 400, 500, 600, 700, 800, 900, 1,000, or more contiguous nucleotides of SEQ ID NOs:3, 4, 5, 7 or other polynucleotides that encode polypeptides shown in SEQ ID NOs:1, 2, 6, 8, 9, 10, 11, 12.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 96, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of *Anaplasma phagocytophilum* polynucleotides that encode biologically functional *Anaplasma phagocytophilum* polypeptides also are *Anaplasma phagocytophilum* polynucleotides.

Polynucleotides of the invention can be isolated from nucleic acid sequences present in, for example, a biological sample, such as blood, serum, saliva, or tissue from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366, 246. A polynucleotide of the invention is operably linked when it is positioned adjacent to or close to one or more expression control elements, which direct transcription and/or translation of the polynucleotide.

Polynucleotides of the invention can be used, for example, as probes or primers, for example, PCR primers, to detect the presence of *Anaplasma phagocytophilum* and/or *Anaplasma platys* polynucleotides in a test sample, such as a biological sample. Probes are molecules capable of interacting with a target nucleic acid, typically in a sequence specific manner, for example, through hybridization. Primers are a subset of probes that can support an enzymatic manipulation and that can hybridize with a target nucleic acid such that the enzymatic manipulation occurs. A primer can be made from any combination of nucleotides or nucleotide derivatives or analogs available in the art that do not interfere with the enzymatic manipulation.

A probe or primer can be about 6, 10, 15, 20, 25, 30, 40, 50, 75, 100, 200, 300, 400, 500, 600, 700, 800, 900, 1,000, or more contiguous nucleotides of SEQ ID NOs:3, 4, 5, 7 or other polynucleotides that encode polypeptides shown in SEQ ID NOs:1, 2, 6, and 8-12.

The hybridization of nucleic acids is well understood in the art and discussed herein. Typically a probe can be made from any combination of nucleotides or nucleotide derivatives or analogs available in the art. The ability of such probes and primers to specifically hybridize to *Anaplasma phagocytophilum* polynucleotide sequences will enable them to be of use in detecting the presence of complementary sequences in a given test sample. Polynucleotide probes and primers of the invention can hybridize to complementary sequences in a test sample such as a biological sample, including saliva, sputum, blood, plasma, serum, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels, and methods for labeling probes and primers, are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging from about 20° C. to about 55° C. The presence of a hybridized complex comprising the probe or primer and a complementary polynucleotide from the test sample indicates the presence of Apl and/or an Apl polynucleotide sequence in the sample.

Antibodies

Antibodies of the invention are antibody molecules that specifically bind to an *Anaplasma phagocytophilum* polypeptide of the invention, variant polypeptides of the invention, or fragments thereof. An antibody of the invention can be specific for an *Anaplasma phagocytophilum* polypeptide, for example, an antibody specific for one or more of SEQ ID NO: 1, 9 or 11. In another embodiment of the invention an antibody is specific for both an *Anaplasma phagocytophilum* polypeptide and an *Anaplasma platys* polypeptide (e.g., an antibody specific for SEQ ID NO:2, 6, 8, 10 or 12). In another embodiment of the invention an antibody is specific for both an *Anaplasma phagocytophilum* polypeptide and another *Anaplasma* polypeptide. One of skill in the art can easily determine if an antibody is specific for an *Anaplasma phagocytophilum* polypeptide or *Anaplasma platys* polypeptide using assays described herein. An antibody of the invention can be a polyclonal antibody, a monoclonal antibody, a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antigen binding antibody fragments include Fab, Fab', Fab'-SH, F(ab')$_2$ and F$_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds," "specifically bind," or "specific for" means that a first antigen, e.g., an *Anaplasma phagocytophilum* polypeptide, recognizes and binds to an antibody of the invention with greater affinity than to other, non-specific molecules. "Specifically binds," "specifically bind," or "specific for" also means a first antibody, e.g., an antibody raised against SEQ ID NOs:1-2, 6, and 8-12, recognizes and binds to SEQ ID NOs:1-2, 6, and 8-12, with greater affinity than to other non-specific molecules. A non-specific molecule is an antigen that shares no common epitope with the first antigen. In a preferred embodiment of the invention a non-specific molecule is not derived from *Anaplasma* sp. An *Anaplasma* sp. is any species of the genus *Anaplasma*. For example, an antibody raised against a first antigen (e.g., a polypeptide) to which it binds more efficiently than to a non-specific antigen can be described as specifically binding to the first antigen. In one embodiment, an antibody or antigen-binding portion thereof specifically binds to a polypeptide of SEQ ID NOs:1, 2, 6, 8, 9, 10, 11, 12 or fragments thereof when it binds with a binding affinity $K_a$ of $10^7$ l/mol or more. Specific binding can be tested using, for example, an enzyme-linked immunosorbant assay (ELISA), a radioimmunoassay (RIA), or a western blot assay using methodology well known in the art.

Antibodies of the invention include antibodies and antigen binding fragments thereof that (a) compete with a reference antibody for binding to SEQ ID NOs:1, 2, 6, 8, 9, 10, 11, 12 or antigen binding fragments thereof; (b) binds to the same epitope of SEQ ID NOs: 1, 2, 6, 8, 9, 10, 11, 12 or antigen binding fragments thereof as a reference antibody; (c) binds to SEQ ID NOs: 1, 2, 6, 8, 9, 10, 11, 12 or antigen binding fragments thereof with substantially the same $K_d$ as a reference antibody; and/or (d) binds to SEQ ID NOs: 1, 2, 6, 8, 9, 10, 11, 12 or fragments thereof with substantially the same off rate as a reference antibody, wherein the reference antibody is an antibody or antigen-binding fragment thereof that specifically binds to a polypeptide of SEQ ID NOs: 1, 2, 6, 8, 9, 10, 11, 12 or antigen binding fragments thereof with a binding affinity $K_a$ of $10^7$ l/mol or more.

One embodiment of the invention provides a first purified polypeptide that specifically binds an antibody, wherein the antibody specifically binds a second purified polypeptide, wherein the second purified polypeptide consists of SEQ ID NO:1, 2, 6, 8, 9, 10, 11, That is, polypeptides of the invention include polypeptides that can specifically bind to antibodies that are capable of specifically binding to a purified polypeptide that consists of SEQ ID NO:1, 2, 6, 8, 9, 10, 11. The first purified polypeptide can consist of at least 10 but less than 300 contiguous amino acids of SEQ ID NO: 1, 2, 6, 8, 9, 10, 11 or 12. The first purified polypeptide can be at least 95% identical to SEQ ID NO: 1, 2, 6, 8, 9, 10, 11 or 12.

Monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing *Anaplasma phagocytophilum*-specific antibodies can be identified using RIA or ELISA and isolated by cloning in semi-solid agar or by limiting dilution. Clones producing *Anaplasma phagocytophilum*-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J. Immunolog. Meth.* 74:307, 1984. Monoclonal antibodies of the invention can also be recombinant monoclonal antibodies. See, e.g., U.S. Pat. No. 4,474,893; U.S. Pat. No. 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., *Nature* 321:522 (1986); Reichmann et al., *Nature* 332:323 (1988); Presta, *Curr. Op. Struct. Biol.* 2:593 (1992)), caninized, canine, or human antibodies. Human antibodies can be made by, for example, direct immortilization, phage display, transgenic mice, or a Trimera methodology, see e.g., Reisener et al., *Trends Biotechnol.* 16:242-246 (1998).

Antibodies that specifically bind *Anaplasma phagocytophilum* antigens (e.g., *Anaplasma phagocytophilum* polypeptides), are particularly useful for detecting the presence of *Anaplasma phagocytophilum* antigens in a sample, such as a serum, blood, plasma, urine, fecal, tissue, or saliva sample from an *Anaplasma phagocytophilum*-infected animal. An immunoassay for *Anaplasma phagocytophilum* antigen can utilize one antibody or several antibodies. An immunoassay for *Anaplasma phagocytophilum* antigen can use, for example, a monoclonal antibody specific for an *Anaplasma phagocytophilum* epitope, a combination of monoclonal antibodies specific for epitopes of one *Anaplasma phagocytophilum* polypeptide, monoclonal antibodies specific for epitopes of different *Anaplasma phagocytophilum* polypeptides, polyclonal antibodies specific for the same *Anaplasma phagocytophilum* antigen, polyclonal antibodies specific for different *Anaplasma phagocytophilum* antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels. Other antibodies of the invention can specifically bind Aph antigens and Apl antigens, or Aph antigens and other *Anaplasma* sp. antigens and can be used as described for Aph above.

Antibodies of the invention or antigen-binding fragments thereof can be bound to a support and used to detect the presence of Apl, *Anaplasma* sp. and/or Aph antigens. Supports include, for example, glass, polystyrene, polypropylene, polyethylene, dextran, nylon, amylases, natural and modified celluloses, polyacrylamides, agaroses and magletite.

Antibodies of the invention can further be used to isolate *Anaplasma* sp., Apl, and/or Aph organisms or antigens by immunoaffinity columns. The antibodies can be affixed to a solid support by, for example, adsorbtion or by covalent linkage so that the antibodies retain their immunoselective activity. Optionally, spacer groups can be included so that the antigen binding site of the antibody remains accessible. The immobilized antibodies can then be used to bind *Anaplasma* organisms or *Anaplasma* antigens from a sample, such as a biological sample including saliva, serum, sputum, blood, urine, feces, cerebrospinal fluid, amniotic fluid, wound exudate, or tissue. The bound *Anaplasma* organisms or *Anaplasma* antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by *Anaplasma* sp., Apl and/or Aph. By measuring the increase or decrease of antibodies specific for Apl, *Anaplasma* sp. and/or Aph in a test sample from an animal, it can be determined whether a particular therapeutic regiment aimed at ameliorating the disorder is effective. Antibodies can be detected and/or quantified using for example, direct binding assays such as RIA, ELISA, or western blot assays.

Methods of Detection

The methods of the invention can be used to detect antibodies or antibody fragments specific for *Anaplasma* sp., Apl, or Aph; *Anaplasma* antigens, Apl antigens, Aph antigens; *Anaplasma* sp. polynucleotides, Apl polynucleotides, Aph polynucleotides; or a combination thereof in a test sample, such as a biological sample, an environmental sample, or a laboratory sample. A test sample can potentially comprise

*Anaplasma* sp. polynucleotides, Apl polynucleotides, Aph polynucleotides, *Anaplasma* sp. polypeptides, Apl polypeptides, Aph polypeptides, antibodies specific for *Anaplasma* sp., antibodies specific for Apl, and/or antibodies specific for Aph, combinations thereof, unrelated antibodies, unrelated polypeptides, unrelated polynucleotides, or none of the above. A biological sample can include, for example, sera, saliva, blood, cells, plasma, urine, feces, or tissue from a mammal such as a horse, cat, dog or human. The test sample can be untreated, precipitated, fractionated, separated, diluted, concentrated, or purified.

In one embodiment methods of the invention comprise contacting one or more polypeptides of the invention with a test sample under conditions that allow polypeptide/antibody complexes, i.e., immunocomplexes, to form. That is, polypeptides of the invention specifically bind to antibodies specific for *Anaplasma* sp., Apl and/or Aph antigens located in the sample. In one embodiment of the invention one or more polypeptides of the invention (e.g., SEQ ID NOs:1, 9, 11 or fragments thereof) specifically bind to antibodies that are specific for Aph antigens and do not specifically bind to Apl antigens. In another embodiment of the invention one or more polypeptides of the invention (e.g., SEQ ID NOs: 2, 6, 8, 10, or 12 or fragments thereof) specifically bind to antibodies that are specific for both Aph and Apl antigens. One of skill in the art is familiar with assays and conditions that are used to detect antibody/polypeptide complex binding. The formation of a complex between polypeptides and anti-*Anaplasma* sp., anti-Apl and/or anti-Aph antibodies in the sample is detected.

Antibodies of the invention can be used in a method of the diagnosis of *Anaplasma* sp., Apl, and/or Aph infection by obtaining a test sample from, e.g., a human or animal suspected of having an *Anaplasma* sp., Apl, and/or Aph infection. The test sample is contacted with antibodies of the invention under conditions enabling the formation of antibody-antigen complexes (i.e., immunocomplexes). One of skill in the art is aware of conditions that enable and are appropriate for formation of antigen/antibody complexes. The amount of antibody-antigen complexes can be determined by methodology known in the art. A level that is higher than that formed in a control sample indicates an *Anaplasma* sp., Apl, and/or Aph infection. A control sample is a sample that does not comprise any Aph and/or Apl polypeptides or antibodies specific for Aph and/or Apl. In one embodiment of the invention the control contains no *Anaplasma* sp. polypeptides or antibodies specific for *Anaplasma* sp. In one embodiment of the invention an antibody is specific for Aph antigens only. In another embodiment of the invention an antibody is specific for both Aph and Apl antigens. Alternatively, a polypeptide of the invention can be contacted with a test sample. Antibodies specific for *Anaplasma* sp., Apl, and/or Aph in a positive test sample will form antigen-antibody complexes under suitable conditions. The amount of antibody-antigen complexes can be determined by methods known in the art.

In one embodiment of the invention, *Anaplasma phagocytophilum* and/or *Anaplasma platys* infection can be detected in a subject. A biological sample is obtained from the subject. One or more purified polypeptides comprising SEQ ID NO: 2, 6, 8, 10, or 12, are contacted with the biological sample under conditions that allow polypeptide/antibody complexes to form. The purified polypeptides can consist of less than about 300 contiguous naturally occurring *Anaplasma phagocytophilum* amino acids. The polypeptide/antibody complexes are detected. The detection of the polypeptide/antibody complexes is an indication that the mammal has an *Anaplasma phagocytophilum* and/or *Anaplasma platys* infection. Because SEQ ID NO: 2, 6, 8, 10, or 12, are specific for both anti-Apl and anti-Aph antibodies, the detected infection can be Aph infection, Apl infection or both Apl and Aph infection. The lack of detection of polypeptide/antibody complexes is an indication that the subject does not have an *Anaplasma phagocytophilum* and/or *Anaplasma platys* infection.

Another embodiment of the invention provides a method of detecting an *Anaplasma phagocytophilum* infection in a subject. The method comprises obtaining a biological sample from the subject and contacting one or more purified polypeptides comprising SEQ ID NO:1, 9 or 11, with the biological sample under conditions that allow polypeptide/antibody complexes to form. The purified polypeptides can consist of less than about 150 contiguous naturally occurring *Anaplasma phagocytophilum* amino acids. The polypeptide/antibody complexes are detected. The detection of the polypeptide/antibody complexes is an indication that the subject has an *Anaplasma phagocytophilum* infection and the lack of detection of the polypeptide/antibody complexes is an indication that the subject does not have an *Anaplasma phagocytophilum* infection.

In one embodiment of the invention, Apl and/or Aph infection can be detected in a subject by about 5 days, 6 days, 7 days, 8 days, 9 days, 10 days, 12 days, 14 days, 15 days, 16 days, 17 days, 18 days, 19 days, 20 days, 21 days or more after the subject acquired the Apl and/or Aph infection. In one embodiment of the invention, Apl and/or Aph infection can be detected in a subject by about 21 days, 20 days, 19 days, 18 days, 17 days, 16 days, 15 days, 14 days, 13 days, 12 days, 11 days, 10 days, 9 days, 8 days, 7 days, 6 days, 5 days, or less after the subject acquired the Aph and/or Apl infection.

In one embodiment of the invention, the polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

In one embodiment of the invention, one or more antibodies of the invention are attached to a solid phase or substrate. A test sample potentially comprising a protein comprising a polypeptide of the invention is added to the substrate. One or more antibodies that specifically bind polypeptides of the invention are added. The antibodies can be the same antibodies used on the solid phase or can be from a different source or species and can be linked to an indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

In another embodiment of the invention, one or more antibodies of the invention are attached to a solid phase or substrate. A test sample potentially comprising a protein comprising a polypeptide of the invention is added to the substrate. Second anti-species antibodies that specifically bind polypeptides of the invention are added. These second antibodies are from a different species than the solid phase antibodies. Third anti-species antibodies are added that specifically bind the second antibodies and that do not specifically bind the solid phase antibodies are added. The third antibodies can comprise an indicator reagent such as an enzyme conjugate. Wash steps can be performed prior to each addition. A chromophor or enzyme substrate is added and color is allowed to develop. The color reaction is stopped and the color can be quantified using, for example, a spectrophotometer.

Assays of the invention include, but are not limited to those based on competition, direct reaction or sandwich-type assays, including, but not limited to enzyme linked immunosorbent assay (ELISA), western blot, IFA, radioimmunoassay (RIA), hemagglutination (HA), fluorescence polarization immunoassay (FPIA), and microtiter plate assays (any assay done in one or more wells of a microtiter plate). One assay of the invention comprises a reversible flow chromatographic binding assay, for example a SNAP® assay. See U.S. Pat. No. 5,726,010.

Assays can use solid phases or substrates or can be performed by immunoprecipitation or any other methods that do not utilize solid phases. Where a solid phase or substrate is used, one or more polypeptides of the invention are directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). In one embodiment of the invention a substrate is sintered, fine particles of polyethylene, commonly known as porous polyethylene, for example, 10-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

In one type of assay format, one or more polypeptides can be coated on a solid phase or substrate. A test sample suspected of containing an anti-*Anaplasma* sp., anti-Apl, and/or anti-Aph antibody or antigen-binding fragment thereof is incubated with an indicator reagent comprising a signal generating compound conjugated to an antibody or antigen-binding antibody fragment specific for *Anaplasma* sp., Apl, and/or Aph for a time and under conditions sufficient to form antigen/antibody complexes of either antibodies of the test sample to the polypeptides of the solid phase or the indicator reagent compound conjugated to an antibody specific for *Anaplasma* sp., Apl, and/or Aph to the polypeptides of the solid phase. The reduction in binding of the indicator reagent conjugated to an anti-*Anaplasma* sp., anti-Apl, and/or anti-Aph antibody to the solid phase can be quantitatively measured. A measurable reduction in the signal compared to the signal generated from, e.g., a confirmed negative *Anaplasma* sp., Apl, and/or Aph test sample indicates the presence of anti-*Anaplasma* sp., anti-Apl, and/or anti-Aph antibody in the test sample. This type of assay can quantitate the amount of anti-*Anaplasma* sp., anti-Apl, and/or anti-Aph antibodies in a test sample.

In another type of assay format, one or more polypeptides of the invention are coated onto a support or substrate. A polypeptide of the invention is conjugated to an indicator reagent and added to a test sample. This mixture is applied to the support or substrate. If antibodies specific for *Anaplasma* sp., Apl, and/or Aph are present in the test sample they will bind the one or more polypeptides conjugated to an indicator reagent and to the one or more polypeptides immobilized on the support. The polypeptide/antibody/indicator complex can then be detected. This type of assay can quantitate the amount of anti-*Anaplasma* sp., anti-Apl, and/or anti-Aph antibodies in a test sample.

In another type of assay format, one or more polypeptides of the invention are coated onto a support or substrate. The test sample is applied to the support or substrate and incubated. Unbound components from the sample are washed away by washing the solid support with a wash solution. If *Anaplasma* sp. specific, Apl specific, and/or Aph specific antibodies are present in the test sample, they will bind to the polypeptide coated on the solid phase. This polypeptide/antibody complex can be detected using a second species-specific antibody that is conjugated to an indicator reagent. The polypeptide/antibody/anti-species antibody indicator complex can then be detected. This type of assay can quantitate the amount of anti-*Anaplasma* sp., anti-Apl, and/or anti-Aph antibodies in a test sample.

The formation of a polypeptide/antibody complex or a polypeptide/antibody/indicator complex can be detected by e.g., radiometric, colorimetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of anti-*Anaplasma* sp., anti-Apl, and/or anti-Aph antibodies in a test sample. Therefore, the methods of the invention can be used to diagnose *Anaplasma* sp., Apl, and/or Aph infection in a patient.

The methods of the invention can also indicate the amount or quantity of anti-*Anaplasma* sp., anti-Apl and/or anti-Aph antibodies in a test sample. With many indicator reagents, such as enzyme conjugates, the amount of antibody present is proportional to the signal generated. Depending upon the type of test sample, it can be diluted with a suitable buffer reagent, concentrated, or contacted with a solid phase without any manipulation. For example, it usually is preferred to test serum or plasma samples that previously have been diluted, or concentrated specimens such as urine, in order to determine the presence and/or amount of antibody present.

The invention further comprises assay kits (e.g., articles of manufacture) for detecting anti-*Anaplasma* sp., anti-Apl and/or anti-Aph antibodies or antigen-binding antibody fragments, *Anaplasma* polypeptides, Apl polypeptides, and/or Aph polypeptides in a sample. A kit comprises one or more polypeptides of the invention and means for determining binding of the polypeptide to anti-*Anaplasma* sp. antibodies, anti-Apl antibodies, and/or or anti-Aph antibodies or antigen-binding antibody fragments in the sample. A kit or article of manufacture can also comprise one or more antibodies or antigen-binding antibody fragments of the invention and means for determining binding of the antibodies or antigen-binding antibody fragments to *Anaplasma* sp. polypeptides, Apl polypeptides, and/or Aph polypeptides in the sample. A kit can comprise a device containing one or more polypeptides or antibodies of the invention and instructions for use of the one or more polypeptides or antibodies for, e.g., the identification of an *Anaplasma* sp., Apl, and/or Aph infection in a mammal. The kit can also comprise packaging material comprising a label that indicates that the one or more polypeptides or antibodies of the kit can be used for the identification of *Anaplasma* sp., Apl, and/or Aph infection. Other components such as buffers, controls, and the like, known to those of ordinary skill in art, can be included in such test kits. The polypeptides, antibodies, assays, and kits of the invention are useful, for example, in the diagnosis of individual cases of *Anaplasma* sp., Apl, and/or Aph infection in a patient, as well as epidemiological studies of *Anaplasma* sp., Apl, and/or Aph outbreaks.

Polypeptides and assays of the invention can be combined with other polypeptides or assays to detect the presence of *Anaplasma* sp. along with other organisms. For example, polypeptides and assays of the invention can be combined with reagents that detect heartworm and/or *Borrelia burgdorferi* and/or *Ehrlichia canis*.

Polynucleotides of the invention can be used to detect the presence of *Anaplasma* sp., Apl and/or Aph polynucleotides in a sample. The polynucleotides can be used to detect *Anaplasma* sp., Apl and/or Aph polynucleotides in a sample by a simple hybridization reaction and can also be used in, e.g., polymerase chain reactions (PCR) such as a real-time PCR reaction. Methods and compositions of the invention can also be used to differentially detect the presence Aph from other *Anaplasma* sp., such as Apl.

PCR assays are well described in the art, including, for example, U.S. Pat. No. 4,683,195; U.S. Pat. No. 4,683,202; U.S. Pat. No. 4,965,188. Generally, polynucleotide primers are annealed to denatured strands of a target nucleic acid. Primer extension products are formed by polymerization of deoxynucleoside triphosphates by a polymerase. PCR then involves repetitive cycles of template nucleic acid denaturation, primer annealing and extension of the annealed primers by the action of a thermostable polymerase. The process results in exponential amplification of the target *Anaplasma* sp. nucleic acids in the test sample, which allows for the detection of target polynucleotides existing in very low concentrations in a sample.

Real-time PCR assays are based on the detection of a signal, e.g., a fluorescent reporter signal. This signal increases in direct proportion to the amount of PCR product in a reaction. Real-time PCR is any amplification technique that makes it possible to monitor the evolution of an ongoing amplification reaction. See, Quantitation of DNA/RNA Using Real-Time PCR Detection, Perkin Elmer Applied Biosystems (1999); PCR Protocols (Academic Press New York, 1989). By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

One embodiment of the invention provides a method for detecting and/or quantifying *Anaplasma* sp., Apl and/or Aph polynucleotides in a test sample. Sense primers and antisense primers can be added to a test sample under conditions suitable for a polymerase chain reaction. The primers hybridize with *Anaplasma* sp., Apl and/or Aph polynucleotides such that an amplification product is formed if *Anaplasma* sp., Apl and/or Aph polynucleotides are present in the test sample. Amplification products are detected and the presence and/or quantity of *Anaplasma* sp., Apl and/or Aph polynucleotides is determined. Amplification products can be detected with a polynucleotide probe that hybridizes, under conditions suitable for a polymerase chain reaction, with an *Anaplasma* sp., Apl and/or Aph polynucleotide sequence. The amplification product can be quantified by measuring a detection signal from the probe and comparing said detection signal to a second probe detection signal from a quantification standard. The quantification standard can be extracted in parallel with the test sample.

One embodiment of the invention provides a method for differentially detecting *Anaplasma platys* polypeptides and *Anaplasma phagocytophilum* polypeptides in a sample. The method comprises:

(a) contacting one or more antibodies that specifically bind to a polypeptide consisting of SEQ ID NO: 2, 6, 8, 10, or 12 with a sample under conditions that allow polypeptide/antibody complexes to form and detecting the polypeptide/antibody complexes; and (b) contacting one or more antibodies that specifically bind to a polypeptide consisting of SEQ ID NO:1, 9, or 11 with the sample under conditions that allow polypeptide/antibody complexes to form and detecting the polypeptide/antibody complexes.

If the polypeptide/antibody complexes are detected in step (a) and in step (b) then the sample contains *Anaplasma phagocytophilum* polypeptides and may also contain *Anaplasma platys* polypeptides. Another test can be run that is specific for *Anaplasma platys*, if desired, in order to determine if *Anaplasma platys* is indeed present. If the polypeptide/antibody complexes are detected in step (a) and are not detected in step (b) then the sample contains *Anaplasma platys* polypeptides and does not contain *Anaplasma phagocytophilum* polypeptides. If the polypeptide complexes are not detected in step (a) and are not detected in step (b) then the sample does not contain *Anaplasma platys* polypeptides and does not contain *Anaplasma phagocytophilum* polypeptides.

Another embodiment of the invention provides a method of detecting antibodies that specifically bind an *Anaplasma platys* polypeptide, an *Anaplasma phagocytophilum* polypeptide, or both an *Anaplasma platys* polypeptide and an *Anaplasma phagocytophilum* polypeptide. The method comprises:

(a) contacting one or more purified polypeptides comprising SEQ ID NO: 2, 6, 8, 10, or 12, with a test sample, under conditions that allow polypeptide/antibody complexes to form and detecting the polypeptide/antibody complexes; and (b) contacting one or more purified polypeptides comprising SEQ ID NO:1, 9, or 11, wherein the purified polypeptide with a test sample, under conditions that allow polypeptide/antibody complexes to form and detecting the polypeptide/antibody complexes.

If the polypeptide/antibody complexes are detected in step (a) and in step (b) then the sample contains antibodies the specifically bind *Anaplasma phagocytophilum* polypeptides and *Anaplasma platys* polypeptides (that is, antibodies that are capable of specifically binding both *Anaplasma platys* and *Anaplasma phagocytophilum* polypeptides) and antibodies that specifically bind only *Anaplasma platys* polypeptides. If the polypeptide/antibody complexes are detected in step (a) and are not detected in step (b) then the sample contains antibodies that specifically bind *Anaplasma platys* polypeptides and *Anaplasma phagocytophilum* polypeptides and does not contain antibodies that specifically bind only *Anaplasma phagocytophilum* polypeptides. If the polypeptide complexes are not detected in step (a) and are not detected in step (b) then the sample does not contain antibodies specific for *Anaplasma platys* polypeptides and does not contain antibodies specific for *Anaplasma phagocytophilum* polypeptides. In one embodiment, the purified polypeptides comprising SEQ ID NO: 2, 6, 8, 10, or 12, consist of less than about 300 contiguous naturally occurring *Anaplasma phagocytophilum* amino acids and the polypeptides comprising SEQ ID NO:1, 9, or 11, consist of less than about 150 contiguous naturally occurring *Anaplasma phagocytophilum* amino acids.

Methods of Treatment, Amelioration, or Prevention of a Disease Caused by Aph and/or Apl Polypeptides, polynucleotides, and antibodies of the invention can be used to treat, ameliorate, or prevent a disease caused by Apl and/or Aph. For example, an antibody, such as a monoclonal antibody of the invention or antigen-binding fragments thereof, can be administered to an animal, such as a human or dog. In one embodiment of the invention an antibody or antigen-binding fragment thereof is administered to an animal in a pharmaceutical composition comprising a pharmaceutically acceptable carrier. A pharmaceutical composition comprises a therapeutically effective amount of an antibody or antigen-binding fragments thereof. A therapeutically effective amount is an amount effective in alleviating the symptoms of an Apl and/or Aph infection or in reducing the amount of Apl and/or Aph organisms in a subject.

Polypeptides or polynucleotides of the invention can be present in an immunogenic composition and used to elicit an immune response in a host. An immunogenic composition or immunogen is capable of inducing an immune response in an animal. An immunogenic polypeptide or polynucleotide composition of the invention is particularly useful in sensitizing an immune system of an animal such that, as one result, an immune response is produced that ameliorates or prevents the effect of Apl and/or Aph infection. The elicitation of an immune response in animal model can be useful to determine, for example, optimal doses or administration routes. Elicitation of an immune response can also be used to treat, prevent, or ameliorate a disease or infection caused by Apl and/or Aph. An immune response includes humoral immune responses or cell mediated immune responses, or a combination thereof. An immune response can also comprise the promotion of a generalized host response, e.g., by promoting the production of defensins.

One embodiment of the invention provides an immunogen that comprises a polypeptide of the invention and one or more additional regions or moieties covalently joined to the polypeptide at the carboxyl terminus or amino terminus. Each region or moiety can, for example, enhance the immune response, facilitate purification of the immunogen, or facilitate polypeptide stability.

Polypeptide stability can be enhanced by adding, for example, polyethylene glycol to the amino or carboxyl terminus of the polypeptide. Other regions or moieties that can improve polypeptide stability include, for example, amino terminus protecting groups such as acetyl, propyl, succinyl, benzyl, benzyloxycarbonyl or t-butyloxycarbonyl and carboxyl terminus protecting groups such as amide, methylamide, and ethylamide.

Polypeptide purification can be enhanced by adding a region or moiety to the carboxyl or amino terminus to facilitate purification. Examples of groups that can be used to facilitate purification include affinity tags such as six-histidine tag, trpE, glutathione and maltose-binding protein.

The ability of a polypeptide to produce an immune response can be enhanced with certain additional regions or moieties. Examples of groups that can be joined to a polypeptide to enhance an immune response include cytokines such as IL-2. See, e.g., Buchan et al., 2000. Molecular Immunology 37:545-552.

The generation of an antibody titer by an animal against Apl and/or Aph can be important in protection from infection and clearance of infection. Detection and/or quantification of antibody titers after delivery of a polypeptide or polynucleotide can be used to identify epitopes that are particularly effective at eliciting antibody titers. Epitopes responsible for a strong antibody response to Apl and/or Aph can be identified by eliciting antibodies directed against Apl and/or Aph polypeptides of different lengths. Antibodies elicited by a particular polypeptide epitope can then be tested using, for example, an ELISA assay to determine which polypeptides contain epitopes that are most effective at generating a strong response. Polypeptides or fusion proteins that contain these epitopes or polynucleotides encoding the epitopes can then be constructed and used to elicit a strong antibody response.

A polypeptide, polynucleotide, or antibody of the invention can be administered to a mammal, such as a mouse, rabbit, guinea pig, macaque, baboon, chimpanzee, human, cow, sheep, pig, horse, dog, cat, or to animals such as chickens or ducks, to elicit antibodies in vivo. Injection of a polynucleotide has the practical advantages of simplicity of construction and modification. Further, injection of a polynucleotide results in the synthesis of a polypeptide in the host. Thus, the polypeptide is presented to the host immune system with native post-translational modifications, structure, and conformation. A polynucleotide can be delivered to a subject as "naked DNA."

Administration of a polynucleotide, polypeptide, or antibody can be by any means known in the art, including intramuscular, intravenous, intrapulmonary, intramuscular, intradermal, intraperitoneal, or subcutaneous injection, aerosol, intranasal, infusion pump, suppository, mucosal, topical, and oral, including injection using a biological ballistic gun ("gene gun"). A polynucleotide, polypeptide, or antibody can be accompanied by a protein carrier for oral administration. A combination of administration methods can also be used to elicit an immune response. Antibodies can be administered at a daily dose of about 0.5 mg to about 200 mg. In one embodiment of the invention antibodies are administered at a daily dose of about 20 to about 100 mg.

Pharmaceutically acceptable carriers and diluents and veterinarily acceptable carries and diluents for therapeutic use are well known in the art and are described in, for example, Remington's Pharmaceutical Sciences, Mack Publishing Co. (A. R. Gennaro ed. (1985)). The carrier should not itself induce the production of antibodies harmful to the host. Such carriers include, but are not limited to, large, slowly metabolized, macromolecules, such as proteins, polysaccharides such as latex functionalized SEPHAROSE®, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells. Liposomes, hydrogels, cyclodextrins, biodegradable nanocapsules, and bioadhesives can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, phosphate buffered saline, Ringer's solution, Hank's solution, glucose, glycerol, dextrose, maltodextrin, ethanol, or the like, singly or in combination, as well as substances such as wetting agents, emulsifying agents, tonicity adjusting agents, detergent, or pH buffering agents. Additional active agents, such as bacteriocidal agents can also be used.

If desired, co-stimulatory molecules, which improve immunogen presentation to lymphocytes, such as B7-1 or B7-2, or cytokines such as MIP1α, GM-CSF, IL-2, and IL-12, can be included in a composition of the invention. Optionally, adjuvants can also be included in a composition. Adjuvants are substances that can be used to nonspecifically augment a specific immune response. Generally, an adjuvant and a polypeptide of the invention are mixed prior to presentation to the immune system, or presented separately, but are presented into the same site of the animal. Adjuvants can include, for example, oil adjuvants (e.g. Freund's complete and incomplete adjuvants) mineral salts (e.g. $Alk(SO_4)_2$; $AlNa(SO_4)_2$, $AlNH_4(SO_4)$, Silica, Alum, $Al(OH)_3$, and $Ca_3(PO_4)_2$), polynucleotides (i.e. Poly IC and Poly AU acids), and certain natural substances (e.g. wax D from *Mycobacterium tuberculosis*, as well as substances found in *Corynebacterium parvum*, *Bordetella pertussis* and members of the genus *Brucella*. Adjuvants which can be used include, but are not limited to MF59-0, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN® (polysorbate) 80 emulsion.

The compositions of the invention can be formulated into ingestible tablets, buccal tablets, troches, capsules, elixirs, suspensions, syrups, wafers, injectable formulations, mouthwashes, dentrifices, and the like. The percentage of one or more polypeptides, polynucleotides, or antibodies of the invention in such compositions and preparations can vary from 0.1% to 60% of the weight of the unit.

Administration of polypeptides, polynucleotides, or antibodies can elicit an immune response in the animal that lasts for at least 1 week, 1 month, 3 months, 6 months, 1 year, or longer. Optionally, an immune response can be maintained in an animal by providing one or more booster injections of the polypeptide, polynucleotide, or antibodies at 1 month, 3 months, 6 months, 1 year, or more after the primary injection. If desired, co-stimulatory molecules or adjuvants can also be provided before, after, or together with the compositions.

A composition of the invention comprising a polypeptide, polynucleotide, antibody, or a combination thereof is administered in a manner compatible with the particular composition used and in an amount that is effective to elicit an immune response as detected by, for example, an ELISA. A polynucleotide can be injected intramuscularly to a mammal, such as a baboon, chimpanzee, dog, or human, at a dose of 1 ng/kg, 10 ng/kg, 100 ng/kg, 1000 ng/kg, 0.001 mg/kg, 0.1 mg/kg, or 0.5 mg/kg. A polypeptide or antibody can be injected intramuscularly to a mammal at a dose of 0.01, 0.05, 0.5, 0.75, 1.0, 1.5, 2.0, 2.5, 5 or 10 mg/kg.

Polypeptides, polynucleotides, or antibodies, or a combination thereof can be administered either to an animal that is not infected with Apl and/or Aph or can be administered to an Apl and/or Aph-infected animal. An immunologically effective amount or therapeutically effective amount means the administration of that amount to an individual, either in a single dose or as part of series, is effective for treatment, amelioration, or prevention of Apl and or Aph infection. The particular dosages of polynucleotide, polypeptides, or antibodies in a composition will depend on many factors including, but not limited to the species, age, gender, concurrent medication, general condition of the mammal to which the composition is administered, and the mode of administration of the composition. An effective amount of the composition of the invention can be readily determined using only routine experimentation.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Sera from Aph or Apl Infected Dogs React Specifically with One or More Antigens from a Hypothetical Aph Open Reading Frame Based on a combination of genomic and protein structural analysis, the hypothetical open reading frame (ORF) Aph__0915 was selected from the genome of Aph (Dunning Hotopp et al. PLoS Genet. 2(2): e21 (February 2006)). Two polynucleotide regions (SEQ ID NOs: 3 and 4) encoding C-terminal fragments of the APH__0915 ORF were PCR amplified using genomic Aph DNA isolated from a blood sample of a Minnesota dog known to be infected with Aph. The PCR products were cloned into an expression vector for protein expression in *E. coli* according to methods well known in the art. Following induction of recombinant protein expression, crude *E. coli* whole cell lysates were analyzed for expression of the recombinant protein, and for reactivity to sera from Aph or Apl infected dogs, using SDS-PAGE electrophoresis and western blotting according to methods well known in the art. The dog sera were obtained from experimentally infected animals, and were used at 1:300 dilution. Crude lysates from *E. coli* vectors comprising SEQ ID NO:3 or SEQ ID NO:4, expressing polypeptides of SEQ ID NO: 2 (wherein the X at position 43 was A; wherein the X at position 113 was D; wherein the X at position 133 was E; and wherein the X at position 138 was absent) or SEQ ID NO:1 (wherein the X at position 52 was D; the X at position 72 was E; and the X at position 77 was absent), respectively, exhibited specific antigen reactivity (above background levels of *E. coli* cross reactivity) to sera from Aph infected dogs. In addition, the crude lysate from clone 13 (expressing polypeptide of SEQ ID NO: 2, wherein the X at position 43 was A; wherein the X at position 113 was D; wherein the X at position 133 was E; and wherein the X at position 138 was absent) exhibited specific antigen reactivity to sera from Apl infected dogs. However, crude lysate from clone 14, expressing polypeptide of SEQ ID NO:1 (wherein the X at position 52 was D; the X at position 72 was E; and the X at position 77 was absent) did not exhibit specific antigen reactivity to sera from Apl infected dogs.

In addition, the full-length APH_0915 ORF (SEQ ID NO:5, having a G at position 667, an A at position 878, an A at position 938, and wherein 953, 954, and 955 are absent) encoding the full-length APH_0915 protein (SEQ ID NO:6 having an A at position 223, a D at position 293, an E at position 313, and no amino acid at position 318), and a polynucleotide region termed "clone 13ext" (SEQ ID NO:7; wherein the N at position 187 was G; wherein the N at position 398 was A; wherein the N at position 458 was A; and wherein the three N's at positions 473-475 were absent) encoding a C-terminal fragment (SEQ ID NO:8; wherein the X at position 63 was A; wherein the X at position 133 was D; wherein the X at position 153 was E; and wherein the X at position 158 was absent) of APH_0915 were PCR cloned and expressed in *E. coli* as described above in this Example. The resulting crude whole cell lysates exhibited specific antigen reactivity to dog serum (from a naturally Aph infected dog exhibiting clinical symptoms of Anaplasmosis) on western blot. Thus, polypeptides comprising SEQ ID NOs:1, 2, 6 and 8 reacted with antibodies from sera of Aph infected dogs. The polypeptide having SEQ ID NO:1 did not react with antibodies from Apl infected dogs, and was therefore specific for Aph only.

Example 2

Nucleotide Sequence and Comparison of Clones 13 and 14

The DNA sequence of clones 13 and 14 were determined. The sequences are aligned with the sequence of APH_0915 (Genbank Acc. No. ABD43857) below. (SEQ ID NOs 5, 4, and 3).

```
APH_0915    1 TTGAGTTTTACAATGTCGAAGTTATCGCTTGACCCTACTCAGGGCTCACATACAGCAGAG
           61 AATATTGCTTGTTCTATCTTTGATATGGTACTTGGTGTAAAGTCCACTGCAAAACTGTTA
          121 GCAGGTACGTGGGCTGGTACAAGCAGCACTATTTGGAAGACAGTAACAGGAGCAGCTTCC
          181 TCAACTAAAGAAGCGTCATCAAAGTCGTATGGAACCCTACGTAGTTCCTTGGGCTCTTCC
          241 GCTTCTAGAAGGATGCTAGGAACTTGCGCTACCGCCGCTCTCTGCTTAACTGCACCTTTG
          301 CTTGGCGCAGCCGCTGCCGGAGCGGCAATAACATGTGCCTTGATAACCATTTGCATGGCT
          361 TTGCTGTTCCTCGTTTTGTACACCGTACTCCACATTGCCTCTCAGATGTTGCGTTGTGCA
          421 TCGCTACTGTTGAGCATGGTATGCAATATCCTGCACAGCACATTCACCGCAACTAAGTCT
          481 TGCCTCGGAGGTAAGTCACCTGCGCGAACAACTGAAGAGCGGGTAGCTGGGGATTTAGAT

APH_0915  541 CACAAAGGGGTGGATTCAGATCGGAAGCATGATGCAGAGAAAACAGAAGAGAAAAAACAT
clone13     1 CACAAAGGGGTGGATTCAGATCGGAAGCATGATGCAGAGAAAACAGAAGAGAAAAAACAT APH_0915  601 GGTTTGGGTAGCCTCTGCAAATCACTCGCGATAAATCTGGTCTCCTTAATGGGAACAGCG
clone13    61 GGTTTGGGTAGCCTCTGCAAATCACTCGCGATAAATCTGGTCTCCTTAATGGGAACAGCG APH_0915  661 CTAGTTACCACACCCATAATACTACTTGCAGTAGTTCTATTAGTGTTGGTGCCAGTATAT
clone13   121 CTAGTTGCCACACCCATAATACTACTTGCAGTAGTTCTATTAGTGTTGGTGCCAGTATAT APH_0915  721 CTGTTATGCGCTACAGTGCACCACATCTATCAAGGAAATTACGAAGATCGCAACAACGAC
clone13   181 CTGTTATGCGCTACAGTGCACCACATCTATCAAGGAAATTACGAAGATCGCAACAACGAC
clone14     1 ---TTATGCGCTACAGTGCACCACATCTATCAAGGAAATTACGAAGATCGCAACAACGAC APH_0915  781 AAAGGTAGCTCCCGTGGCGGCGGTACTACATATTATCCAATGACAATGTCTGCAAGTGCT
clone13   241 AAAGGTAGCTCCCGTGGCGGCGGTACTACATATTATCCAATGACAATGTCTGCAAGTGCT
clone14    58 AAAGGTAGCTCCCGTGGCGGCGGTACTACATATTATCCAATGACAATGTCTGCAAGTGCT APH_0915  841 TCTGAAGAGTCCCTTAGCAGCATAATATCTGAAGGAGGTTTGAGTAAGACATCGCTACCA
clone13   301 TCTGAAGAGTCCCTTAGCAGCATAATATCTGAAGGAGATTTGAGTAAGACATCGCTACCA
clone14   118 TCTGAAGAGTCCCTTAGCAGCATAATATCTGAAGGAGATTTGAGTAAGACATCGCTACCA APH_0915  901 AGTTACTCCGCAGCCACTGCTACAGGTACTGGAAATGCAACTGGTGAGGTTTTTTCACAT
clone13   361 AGTTACTCCGCAGCCACTGCTACAGGTACTGGAAATGCAACTGGTGAGGTTT---CACAT
clone14   178 AGTTACTCCGCAGCCACTGCTACAGGTACTGGAAATGAAACTGGTGAGGTTT---CACAT APH_0915  961 TCTCATTCATCTGGTAAAAGTAGCAGCAAACCAGAATCTCGCCCTGAGAGCAATCTACAG
clone13   418 TCTCATTCATCTGGTAAAAGTAGCAGCAAACCAGAATCTCGCCCTGAGAGCAATCTACAG
clone14   235 TCTCATTCATCTGGTAAAAGTAGCAGCAAACCAGAATCTCGCCCTGAGAGCAATCTACAG APH_0915 1021 AATGTGGTAGCAGAAACCATGTCGCAGCAACAAAGGAGCGTCTCC         (SEQ ID NO: 5)
clone13   478 AATGTGGTAGCAGAAACCATGTCGCAGCAACAAAGGAGCGTCTCC         (SEQ ID NO: 4)
clone14   295 AATGTGGTAGCAGAAACCATGTCGCAGCAACAAAGGAGCGTCTCC         (SEQ ID NO: 3)
```

The underlining represents differences between the clone 13/clone 14 sequences and the Aph_0915 genomic sequence. Furthermore, the DNA sequence of clone 13ext and that of a full-length clone were determined, revealing the same sequence differences (as compared to Genbank Acc. No. ABD43857) identified in clone 13 and clone 14.

Example 3

Clone 13, but not Clone 14, Detects Apl in Field Samples

An experiment was conducted to determine the reactivity of SEQ ID NO:1 (clone 14) (wherein the X at position 52 was D; the X at position 72 was E; and the X at position 77 was absent) or SEQ ID NO:2 (clone 13) (wherein the X at position 43 was A; wherein the X at position 113 was D; wherein the X at position 133 was E; and wherein the X at position 138 was absent) with sera from Apl-infected dogs on western blots (Table 2). Sera from thirteen dogs known to be infected with Apl were tested. These sera were derived from dogs living on the Hopi Indian Reservations, Arizona, where only Apl (not Aph) is prevalent. See, Table 2.

SEQ ID NO:1 (wherein the X at position 52 was D; the X at position 72 was E; and the X at position 77 was absent) was not reactive with any of the 13 Apl positive samples. Thus, SEQ ID NO:1 is specific for anti-Aph antibodies (see, Example 1) in that it does not react with anti-Apl antibodies.

SEQ ID NO:2 (wherein the X at position 43 was A; wherein the X at position 113 was D; wherein the X at position 133 was E; and wherein the X at position 138 was absent) was reactive with all 13 of the Apl positive samples. Thus, SEQ ID NO:2 can detect both anti-Aph (see, examples 1 and 5) and anti-Apl antibodies. See, Table 2.

TABLE 2

| Hopi Apl Sample | clone 14 western | clone 13 western |
|---|---|---|
| HP 118 | − | + |
| HP 127 | − | + |
| HP 136 | − | + |
| HP 141 | − | + |
| HP 166 | − | + |
| HP 168 | − | + |
| HP 170 | − | + |
| HP 186 | − | + |
| HP 199 | − | + |
| HP 214 | − | + |
| HP 230 | − | + |
| HP 235 | − | + |
| HP 242 | − | + |

Example 4

Detection of Aph by Clone 14 with Field Samples

Fifty canine serum samples from an area of Minnesota where only Aph (not Apl) is prevalent, were tested in this experiment. Of these 50 samples, 47 were known Aph positives, and 3 samples were known Aph negatives. Sensitivity of SEQ ID NO:1 (clone 14; wherein the X at position 52 was D; the X at position 72 was E; and the X at position 77 was absent), for Aph was tested by western blots (as described above). Out of the 47 known positive samples, 39 were positive on the clone 14 western assay. Out of the 3 known negative samples, 2 were negative, and 1 positive, on the clone 14 western assay (Table 3). Thus, the SEQ ID NO:1 assay showed 83% (39/471 sensitivity for Aph positive samples (Table 31.

TABLE 3

| | Clone 14 western assay | |
|---|---|---|
| | Positive | Negative |
| Aph Positive | 39 | 8 |
| Aph Negative | 1 | 2 |

Example 5

Detection of Aph Antibody by SEQ ID NO:2 (Clone 13)

An experiment was conducted to determine whether a polypeptide comprising SEQ ID NO:2 (clone 13) (wherein the X at position 43 was A; wherein the X at position 113 was D; wherein the X at position 133 was E; and wherein the X at position 138 was absent) can detect Aph antibodies in sera from dogs exhibiting clinical symptoms of acute Anaplasmosis.

A purified preparation of a recombinant polypeptide comprising SEQ ID NO:2 (wherein the X at position 43 was A; wherein the X at position 113 was D; wherein the X at position 133 was E; and wherein the X at position 138 was absent) was coated on Immulon® 4 wells overnight at 3 ug/mL in carbonate buffer, pH 9.6. The wells were washed 3× with PBST and blocked with 1% BSA in PBS for 1 h. Test samples (dog sera) diluted 1:200 in PRRS Sample Diluent, were added to the wells and incubated for 1 h. The wells were washed 6× with HW PetChek® Wash Buffer. Anti-dog (H+L):HRPO 1:4000 in Enzyme Conjugate Diluent was added and incubated for 1 h. The wells were washed 6× with HW PetChek® Wash Buffer. 50 µl TMB was added for 10 min and then of 50 µl stop solution was added. The wells were read at A650.

This indirect ELISA was performed with sera from Aph infected dogs exhibiting clinical symptoms of acute anaplasmosis. Four random samples from normal dogs were tested as negative controls to determine a cut off OD value (cut off=mean+2×SD). Test samples producing OD values above this cutoff value were deemed "positives" and are represented by "+" in Table 4.

TABLE 4

| ID | Clone 13 |
|---|---|
| ME-485 | + |
| ME-487 | + |
| ME-560 | + |
| ME-562 | + |
| ME-568 | + |
| ME-601 | + |
| ME-616 | + |
| ME-631 | + |
| ME-661 | + |
| ME-670 | + |
| ME-699 | + |
| ME-703 | + |
| ME-710 | + |
| ME-716 | + |
| ME-734 | + |
| ME-741 | + |
| ME-748 | − |
| ME-753 | + |

TABLE 4-continued

| ID | Clone 13 |
|---|---|
| ME-476 | + |
| ME-534 | + |
| ME-630 | + |
| ME-639 | − |
| ME-653 | − |
| ME-691 | − |
| ME-700 | + |
| ME-746 | + |

Of the 26 samples tested, 22 samples were positive in the ELISA using SEQ ID NO:2. These results demonstrate that a polypeptide comprising SEQ ID NO:2 can detect Aph antibodies in sera from dogs having symptoms of acute anaplasmosis with high sensitivity.

Example 6

Detection of Aph Antibody with Synthetic Polypeptides

Synthetic polypeptides having an amino acid sequence of SEQ ID NO:9, SEQ ID NO:10, or SEQ ID NO:11 were evaluated for their ability to detect Aph antibody in an indirect ELISA assay. Each of the three peptides was coated on microtiter plates in serial dilution (0.0-0.5 ul/ml) and tested for reactivity to serum obtained from a naturally infected dog (this dog exhibited symptoms of acute anaplasmosis, and was a known seropositive for Aph infection). A pooled sample from 10 normal dogs was used as negative control.

Briefly, synthetic polypeptides having amino acid sequences of SEQ ID NO:9 (p37-1), SEQ ID NO:10 (p37-2), or SEQ ID NO:11 (p37-3; wherein the X at position 1 was C; wherein the X at position 2 was E; and wherein the X at position 7 was absent), were coated onto Immulon® 4 wells overnight in carbonate buffer, pH 9.6. The wells were washed 2× with HW PetChek® Wash Buffer, followed by blocking for 2 hours with 2% TWEEN® (polysorbate) 20, 2.5% Sucrose in 0.1M Tris (pH 7.6), and dried overnight. Dog serum diluted (1:100) in IBR Conjugate Diluent (IDEXX Laboratories) was added to the wells and incubated for 45 min. The wells were washed 5× with HW PetChek® Wash Buffer. Rabbit anti-dog antibody (H+L) conjugated to HRPO diluted (1:2000) in IBR Conjugate Diluent was added and incubated for 45 min. The wells were washed 6× with HW PetChek® Wash Buffer. 60 μl TMB was added for 10 min and then of 50 μl stop solution was added. The optical density (OD) was read at A650 (Table 5).

TABLE 5

| peptide | peptide concentration (ug/ml) | Aph dog serum (OD) | normal dog serum (OD) |
|---|---|---|---|
| p37-1 | 0 | 0.28 | 0.15 |
|  | 0.06 | 0.56 | 0.15 |
|  | 0.125 | 0.59 | 0.16 |
|  | 0.25 | 0.58 | 0.18 |
|  | 0.5 | 0.72 | 0.19 |
| p37-2 | 0 | 0.30 | 0.17 |
|  | 0.06 | 0.48 | 0.16 |
|  | 0.125 | 1.06 | 0.16 |
|  | 0.25 | 1.93 | 0.19 |
|  | 0.5 | 2.28 | 0.22 |
| p37-3 | 0 | 0.30 | 0.15 |
|  | 0.06 | 0.45 | 0.15 |
|  | 0.125 | 0.56 | 0.15 |
|  | 0.25 | 0.82 | 0.19 |
|  | 0.5 | 1.26 | 0.37 |

The results in Table 5 show that all three synthetic polypeptides tested (SEQ ID NO:9 (p37-1), SEQ ID NO:10 (p37-2), SEQ ID NO:11 (p37-3) (wherein the X at position 1 was C; wherein the X at position 2 was E; and wherein the X at position 7 was absent)) were reactive with sera from a symptomatic, Aph-infected dog. At polypeptide concentrations ranging from 0.125 to 0.5 ug/ml, the strongest signal was obtained with SEQ ID NO:10 (p37-2).

Example 7

Detection of Aph Antibody by Polypeptide p37-2

An experiment was conducted to determine whether a synthetic polypeptide comprising SEQ ID NO:10 (p37-2) can detect Aph antibodies in sera from dogs exhibiting clinical symptoms of acute Anaplasmosis.

An ELISA was performed as described herein in Example 6, except the synthetic peptide was coated at 0.5 ug/ml. The test samples were sera from Aph infected dogs exhibiting clinical symptoms of acute anaplasmosis. Four random samples from normal dogs were tested as negative controls to determine a cut off OD value (cut off=mean+2×SD). Test samples producing OD values above this cutoff value were deemed "positives" and are represented by "+" in Table 6.

TABLE 6

| ID | P37-2 |
|---|---|
| ME-485 | + |
| ME-487 | + |
| ME-560 | + |
| ME-562 | + |
| ME-568 | + |
| ME-601 | + |
| ME-616 | + |
| ME-631 | + |
| ME-661 | + |
| ME-670 | + |
| ME-699 | + |
| ME-703 | + |
| ME-710 | + |
| ME-716 | + |
| ME-734 | + |
| ME-741 | + |
| ME-748 | − |
| ME-753 | + |
| ME-476 | + |
| ME-534 | + |
| ME-630 | + |
| ME-639 | − |
| ME-653 | − |
| ME-691 | − |
| ME-700 | + |
| ME-746 | + |

Of the 26 samples tested, 22 samples were positive in the ELISA using SEQ ID NO:10. These results demonstrate that a polypeptide comprising SEQ ID NO:10 can detect Aph antibodies in sera from dogs having symptoms of acute anaplasmosis with high sensitivity.

Example 8

Early Detection of Aph Antibody in Sera of Experimentally Infected Dogs by Peptide p37-2

An indirect ELISA was conducted to determine the time course of seroreactivity to peptide p37-2 (SEQ ID NO:10) following experimental Aph infection (Table 7). The assay was performed according to the procedure as described herein in Example 6, except the synthetic peptide was coated at 0.5 ug/ml. Canine sera were obtained from two experimentally infected dogs. One of these dogs was infected with Aph strain Webster (a human isolate), and developed thrombocytopenia which reached its worst levels at day 10. Lymph node swelling was first detected at day 7. The second dog was infected with Aph strain MN98E.4 (a canine isolate), and developed thrombocytopenia which reached its worst levels at day 14. Mild lymph node swelling was first detected at day 4, and fever peaked at day 9 in the second dog. Blood samples were taken at various time points post-infection. Aph seroreactivity was first detected at day 7 in sera from the dog infected with strain Webster, and at day 14 in sera from the dog infected with strain MN98E.4 (Table 7). Thus, p37-2 can detect of Aph infection in dogs at about 7-14 days post-infection. Since the onset of clinical symptoms of acute anaplasmosis typically occurs within 1-2 weeks from the time of infection, p37-2 is useful as a diagnostic tool as early as the time of onset of symptoms.

TABLE 7

| Aph strain | days post-infection | p37-2 ELISA cut-off = 0.21 |
| --- | --- | --- |
| Webster | 0 | − |
|  | 2 | − |
|  | 4 | − |
|  | 7 | + |
|  | 10 | + |
|  | 14 | + |
|  | 17 | + |
|  | 21 | + |
|  | 24 | + |
| MN98E.4 | 0 | − |
|  | 2 | − |
|  | 4 | − |
|  | 7 | − |
|  | 10 | − |
|  | 14 | + |
|  | 17 | + |
|  | 21 | + |
|  | 24 | + |

Example 9

Detection of Apl Antibody by Polypeptide p37-2

An experiment was conducted to determine whether a synthetic polypeptide comprising SEQ ID NO:10 (p37-2) can detect Apl antibodies in sera from two experimentally infected dogs. The assay was performed as described herein in Example 6, except the synthetic peptide was coated at 0.5 ug/ml. Samples from 10 normal dogs were tested as negative controls to determine a cut off OD value (cut off=mean+2× SD). Test samples producing OD values above this cutoff value were deemed "positives" and are represented by "+" in Table 7.

TABLE 7

| Canine ID | Days Post Infection | p37-2 |
| --- | --- | --- |
| A5 | 3 | − |
|  | 7 | − |
|  | 10 | + |
|  | 14 | + |
|  | 17 | + |
|  | 21 | + |
|  | 24 | + |
|  | 28 | + |
|  | 35 | + |
|  | 42 | + |
|  | 49 | + |
|  | 56 | + |
|  | 63 | + |
|  | 71 | + |
|  | 79 | + |
| A6 | 3 | − |
|  | 7 | − |
|  | 10 | + |
|  | 13 | + |
|  | 17 | + |
|  | 21 | + |
|  | 24 | + |
|  | 28 | + |
|  | 34 | + |
|  | 42 | + |
|  | 49 | + |
|  | 56 | + |
|  | 62 | + |
|  | 70 | + |
|  | 78 | + |

Sera from both dogs were positive starting at day 10 post-infection in the ELISA using SEQ ID NO:10. These results demonstrate that a polypeptide comprising SEQ ID NO:10 can detect Apl antibodies in sera from Apl infected dogs, as early as 10 days post-infection.

While the working examples provided herein were performed on sera from dogs, a skilled artisan will appreciate that the compositions and methods disclosed herein are readily applicable to the detection of Aph and/or Apl in other host species of Aph and/or Apl, such as for example humans, horses, cats, deer and ruminants.

We claim:

1. A method of detecting antibodies that specifically bind an *Anaplasma phagocytophilum* polypeptide or an *Anaplasma platys* polypeptide in a test sample, comprising:

(a) contacting a purified polypeptide at least 95% identical to SEQ ID NO:10, wherein, optionally, the purified polypeptide is linked to an indicator reagent, an amino acid spacer, an amino acid linker, a signal sequence, a stop transfer sequence, a transmembrane domain, a protein purification ligand, a heterologous protein, one or more additional polypeptides comprising SEQ ID NO:1, 2, 6, 8, 9, 10, 11, 12, or a combination thereof, with the test sample, under conditions that allow polypeptide/antibody complexes to form;

(b) detecting the polypeptide/antibody complexes;

wherein the detection of the polypeptide/antibody complexes is an indication that antibodies specific for an *Anaplasma phagocytophilum* polypeptide or an *Anaplasma platys* polypeptide are present in the test sample.

2. The method of claim 1, further comprising contacting the complexes of step (a) with an indicator reagent prior to the performance of step (b).

3. The method of claim 1, wherein the amount of antibodies in the test sample is determined.

4. The method of claim 1, wherein the purified polypeptide is attached to a substrate.

5. A method of detecting an *Anaplasma phagocytophilum* infection or an *Anaplasma platys* infection in a subject comprising:

(a) obtaining a biological sample from the subject;

(b) contacting a purified polypeptide that is at least 95% identical to SEQ ID NO:10 wherein, optionally, the purified polypeptide is linked to an indicator reagent, an amino acid spacer, an amino acid linker, a signal sequence, a stop transfer sequence, a transmembrane domain, a protein purification ligand, a heterologous protein, one or more additional polypeptides comprising SEQ ID NO:1, 2, 6, 8, 9, 10, 11, 12, or a combination thereof, with the biological sample under conditions that allow polypeptide/antibody complexes to form;

(c) detecting the polypeptide/antibody complexes;

wherein the detection of the polypeptide/antibody complexes is an indication that the subject has an *Anaplasma phagocytophilum* infection or an *Anaplasma platys* infection.

6. A method of detecting antibodies that specifically bind both *Anaplasma platys* polypeptides and *Anaplasma phagocytophilum* polypeptides, comprising:

(a) contacting a purified polypeptide that is at least 95% identical to SEQ ID NO:10, with a test sample, under conditions that allow polypeptide/antibody complexes to form;

(b) detecting the polypeptide/antibody complexes;

wherein the detection of the polypeptide/antibody complexes is an indication that antibodies specific for *Anaplasma platys* and/or *Anaplasma phagocytophilum* are present in the test sample.

7. The method of claim 6, further comprising contacting the complexes of step (a) with an indicator reagent prior to the performance of step (b).

8. The method of claim 6, wherein the amount of antibodies in the test sample is determined.

9. The method of claim 6, wherein the purified polypeptide is attached to a substrate.

10. The method of claim 6, wherein the purified are polypeptide is linked to an indicator reagent, an amino acid spacer, an amino acid linker, a signal sequence, a stop transfer sequence, a transmembrane domain, a protein purification ligand, a heterologous protein, one or more additional polypeptides comprising SEQ ID NO:1, 2, 6, 8, 9, 10, 11, 12, or a combination thereof.

11. A method of detecting an *Anaplasma phagocytophilum* and/or *Anaplasma platys* infection in a subject comprising:

(a) obtaining a biological sample from the subject;

(b) contacting a purified polypeptide comprising SEQ ID NO: 10, with the biological sample under conditions that allow polypeptide/antibody complexes to form;

(c) detecting the polypeptide/antibody complexes;

wherein the detection of the polypeptide/antibody complexes is an indication that the subject has an *Anaplasma phagocytophilum* and/or *Anaplasma platys* infection.

12. A method of detecting antibodies that specifically bind art *Anaplasma platys* polypeptides, *Anaplasma phagocytophilum* polypeptides, or both *Anaplasma platys* polypeptides and *Anaplasma phagocytophilum* polypeptides, comprising:

(a) contacting a purified polypeptide at least 95% identical to SEQ ID NO:10 with a test sample, under conditions that allow polypeptide/antibody complexes to form and detecting the polypeptide/antibody complexes; and (b) contacting one or more purified polypeptides at least 95% identical to SEQ ID NO:1, 9, or 11, wherein the purified polypeptides consist of less than about 150 contiguous naturally occurring *Anaplasma phagocytophilum* amino acids, with a test sample, under conditions that allow polypeptide/antibody complexes to form and detecting the polypeptide/antibody complexes;

wherein if the polypeptide/antibody complexes are detected in step (a) and in step (b) then the sample contains antibodies that specifically bind *Anaplasma phagocytophilum* polypeptides and *Anaplasma platys* polypeptides and antibodies that specifically bind only *Anaplasma platys* polypeptides; wherein if the polypeptide/antibody complexes are detected in step (a) and are not detected in step (b) then the sample contains antibodies that specifically bind *Anaplasma platys* polypeptides and *Anaplasma phagocytophilum* polypeptides and does not contain antibodies that specifically bind only *Anaplasma phagocytophilum* polypeptides; wherein if the polypeptide complexes are detected in step (b) and are not detected in step (a), then the sample contains antibodies that specifically bind only *Anaplasma phagocytophilum* polypeptides; and wherein if the polypeptide complexes are not detected in step (a) and are not detected in step (b) then the sample does not contain antibodies specific for *Anaplasma platys* polypeptides and does not contain antibodies specific for *Anaplasma phagocytophilum* polypeptides.

13. The method of claim 5, further comprising contacting the complexes of step (b) with an indicator reagent prior to the performance of step (c).

14. The method of claim 5, wherein the purified polypeptide is attached to a substrate.

15. The method of claim 12, wherein the amount of antibodies in the test sample is determined.

16. The method of claim 12, wherein the purified polypeptide is attached to a substrate.

17. The method of claim 12, wherein the purified polypeptides are linked to an indicator reagent, an amino acid spacer, an amino acid linker, a signal sequence, a stop transfer sequence, a transmembrane domain, a protein purification ligand, a heterologous protein, one or more additional polypeptides comprising SEQ ID NO:1, 2, 6, 8, 9, 10,11, 12, or a combination thereof.

18. The method of claim 11, further comprising contacting the complexes of step (b) with an indicator reagent prior to the performance of step (c).

19. The method of claim 11, wherein the amount of antibodies in the test sample is determined.

20. The method of claim 11, wherein the purified polypeptide is attached to a substrate.

21. The method of claim 11, wherein the purified polypeptide is linked to an indicator reagent, an amino acid spacer, an amino acid linker, a signal sequence, a stop transfer sequence, a transmembrane domain, a protein purification ligand, a heterologous protein, one or more additional polypeptides comprising SEQ ID NO:1, 2, 6, 8, 9, 10, 11, 12, or a combination thereof.

\* \* \* \* \*